United States Patent
Lu et al.

(10) Patent No.: US 11,944,702 B2
(45) Date of Patent: Apr. 2, 2024

(54) SKIN CARE COMPOSITION AND METHOD OF MAKING A SKIN CARE COMPOSITION

(71) Applicant: L'OREAL, Paris (FR)

(72) Inventors: Gloria Lu, Rahway, NJ (US); Donna McCann, Oxford, NJ (US); Patricia Brieva, Manalapan, NJ (US)

(73) Assignee: L'OREAL, Paris (FR)

( * ) Notice: Subject to any disclaimer, the term of this patent is extended or adjusted under 35 U.S.C. 154(b) by 578 days.

(21) Appl. No.: 16/850,758

(22) Filed: Apr. 16, 2020

(65) Prior Publication Data

US 2020/0253853 A1 Aug. 13, 2020

Related U.S. Application Data

(60) Division of application No. 15/477,901, filed on Apr. 3, 2017, now Pat. No. 10,668,001, and a
(Continued)

(51) Int. Cl.
*A61K 8/67* (2006.01)
*A61K 8/34* (2006.01)
(Continued)

(52) U.S. Cl.
CPC .............. *A61K 8/675* (2013.01); *A61K 8/347* (2013.01); *A61K 8/365* (2013.01); *A61K 8/42* (2013.01);
(Continued)

(58) Field of Classification Search
None
See application file for complete search history.

(56) References Cited

U.S. PATENT DOCUMENTS

| 4,813,785 A | 3/1989 | Miller |
| 4,871,262 A | 10/1989 | Krauss et al. |

(Continued)

FOREIGN PATENT DOCUMENTS

| EP | 0443741 A1 | 8/1991 | |
| FR | 2946254 A1 * | 12/2010 | ............. A61K 36/48 |

(Continued)

OTHER PUBLICATIONS

English translation of FR 2946254 A1 (Year: 2010).*
(Continued)

*Primary Examiner* — Nicole P Babson
(74) *Attorney, Agent, or Firm* — McNees Wallace & Nurick LLC

(57) ABSTRACT

A customized skin care composition. The skin care composition includes a base composition comprising one of an aqueous alcohol composition or an aqueous emulsion. The skin care composition further includes at least two booster compositions selected from the group consisting of a first grade exfoliating agent; a second grade exfoliating agent, the second grade exfoliating agent providing greater exfoliating than the first grade exfoliating agent; a first grade whitening agent; a second grade whitening agent, the second grade whitening agent providing greater whitening than the first grade whitening agent; a first grade anti-aging agent; and a second grade anti-aging agent, the second grade anti-aging agent providing greater anti-aging effects than the first grade anti-aging agent. The base composition and the at least two booster compositions have been mixed to form a composition that is stable and has efficacious concentrations of active ingredients corresponding to skin conditions of a consumer.

9 Claims, 14 Drawing Sheets

Related U.S. Application Data continuation-in-part of application No. 15/477,929, filed on Apr. 3, 2017, now Pat. No. 10,902,492, and a continuation-in-part of application No. 15/477,965, filed on Apr. 3, 2017, now Pat. No. 10,776,800, and a continuation of application No. 16/580,498, filed on Sep. 24, 2019, now Pat. No. 11,235,299, and a continuation of application No. 15/477,992, filed on Apr. 3, 2017, now Pat. No. 10,464,030.

(51) Int. Cl.

| | |
|---|---|
| A61K 8/365 | (2006.01) |
| A61K 8/42 | (2006.01) |
| A61K 8/44 | (2006.01) |
| A61K 8/49 | (2006.01) |
| A61K 8/60 | (2006.01) |
| A61Q 19/00 | (2006.01) |
| A61Q 19/02 | (2006.01) |
| A61Q 19/08 | (2006.01) |
| B01F 29/10 | (2022.01) |
| B01F 33/84 | (2022.01) |
| B01F 35/71 | (2022.01) |
| B01F 101/21 | (2022.01) |
| G06Q 30/0601 | (2023.01) |
| G16H 20/13 | (2018.01) |
| G16H 20/70 | (2018.01) |
| G16H 40/60 | (2018.01) |

(52) U.S. Cl.
CPC .............. *A61K 8/44* (2013.01); *A61K 8/494* (2013.01); *A61K 8/498* (2013.01); *A61K 8/602* (2013.01); *A61K 8/671* (2013.01); *A61Q 19/02* (2013.01); *A61Q 19/08* (2013.01); *G16H 20/13* (2018.01); *G16H 20/70* (2018.01); *G16H 40/60* (2018.01); *A61K 2300/00* (2013.01); *A61K 2800/28* (2013.01); *A61K 2800/80* (2013.01); *A61K 2800/87* (2013.01); *A61K 2800/882* (2013.01); *A61Q 19/00* (2013.01); *B01F 29/10* (2022.01); *B01F 33/8442* (2022.01); *B01F 35/715* (2022.01); *B01F 35/716* (2022.01); *B01F 35/717* (2022.01); *B01F 2101/21* (2022.01); *G06Q 30/0621* (2013.01)

(56) References Cited

U.S. PATENT DOCUMENTS

| | | | |
|---|---|---|---|
| 4,967,938 A | 11/1990 | Hellenberg | |
| 5,078,302 A | 1/1992 | Hellenberg | |
| 5,119,973 A | 6/1992 | Miller et al. | |
| 5,368,196 A | 11/1994 | Hellenberg et al. | |
| 5,474,211 A | 12/1995 | Hellenberg | |
| 5,551,779 A | 9/1996 | Gantner et al. | |
| 5,622,692 A | 4/1997 | Rigg et al. | |
| 5,637,275 A | 6/1997 | Carey et al. | |
| 5,785,960 A | 7/1998 | Rigg et al. | |
| 5,903,465 A | 5/1999 | Brown | |
| 5,938,080 A | 8/1999 | Haaser et al. | |
| 6,177,093 B1 | 1/2001 | Lombardi et al. | |
| 6,284,228 B1 | 9/2001 | Markowitz et al. | |
| 6,437,866 B1 | 8/2002 | Flynn | |
| 6,492,326 B1* | 12/2002 | Robinson ............... A61K 8/675 |
| | | | 514/18.6 |
| 6,510,366 B1 | 1/2003 | Murray et al. | |
| 6,524,598 B2 | 2/2003 | Sunkel et al. | |
| 6,585,012 B1 | 7/2003 | Tovino | |
| 6,719,453 B2 | 4/2004 | Cosman et al. | |
| 6,782,307 B2 | 8/2004 | Wilmott et al. | |
| 6,935,386 B2 | 8/2005 | Miller et al. | |
| 7,185,789 B2 | 3/2007 | Mink et al. | |
| 7,654,416 B2 | 2/2010 | Buining et al. | |
| 7,665,398 B2 | 2/2010 | Gerber | |
| 8,564,778 B1 | 10/2013 | Igarashi | |
| 8,593,634 B1 | 11/2013 | Igarashi | |
| 9,145,884 B2 | 9/2015 | Solera et al. | |
| 9,442,494 B2 | 9/2016 | Igarashi | |
| 9,858,685 B2 | 1/2018 | Nichol et al. | |
| 9,918,931 B2 | 3/2018 | Dersh et al. | |
| 10,231,911 B2 | 3/2019 | Dersh et al. | |
| 2002/0082745 A1 | 6/2002 | Wilmott et al. | |
| 2002/0179639 A1 | 12/2002 | Bartholomew et al. | |
| 2003/0065552 A1* | 4/2003 | Rubinstenn ........... A61B 5/0059 |
| | | | 705/26.7 |
| 2003/0090176 A1 | 5/2003 | Bartholomew et al. | |
| 2005/0021174 A1 | 1/2005 | Wilmott et al. | |
| 2005/0092772 A1 | 5/2005 | Miller et al. | |
| 2007/0014748 A1* | 1/2007 | Bernard ................ A61K 31/17 |
| | | | 424/70.14 |
| 2014/0081463 A1 | 3/2014 | Igarashi | |
| 2015/0021356 A1 | 1/2015 | Witchell et al. | |
| 2016/0107133 A1 | 4/2016 | Sugino et al. | |
| 2018/0280277 A1 | 10/2018 | Lu et al. | |
| 2018/0280905 A1 | 10/2018 | Orsita et al. | |
| 2018/0284729 A1 | 10/2018 | Orsita et al. | |
| 2018/0285952 A1 | 10/2018 | Lu et al. | |

FOREIGN PATENT DOCUMENTS

| | | |
|---|---|---|
| JP | 2008532100 A | 8/2008 |
| JP | 2009540457 A | 11/2009 |
| WO | 2000064570 A1 | 8/1991 |
| WO | 2009137277 A2 | 11/2009 |
| WO | 2014095204 A2 | 6/2014 |

OTHER PUBLICATIONS

Notice of Alowance issued by the USPTO dated May 13, 2020 for U.S. Appl. No. 15/477,965.

Office Action issued to Japanese counterpart application JP2019-554370 dated Oct. 5, 2021.

International Search Report for PCT/US2018/025111 dated Jun. 22, 2018.

https://www.ricaud.com/en/beauty-advice/facial-care-diagnosis.htm, Pierre Ricaud, downloaded from the Internet Jun. 13, 2017.

https://www.codageparis.com/en/myscan/index/step0/, Codate Paris, downloaded from the Internet Jun. 13, 2017.

Non-Final Office Action issued by USPTO dated Dec. 21, 2018 for U.S. Appl. No. 15/477,992.

Notice of Allowance issued by USPTO dated Jun. 20, 2019 for U.S. Appl. No. 15/477,992.

Non-Final Office Action issued by the USPTO dated Dec. 30, 2019 for U.S. Appl. No. 15/477,965.

Notice of Allowance issued by the USPTO dated Apr. 27, 2020 for U.S. Appl. No. 15/477,965.

Non-Final Office Action issued by the USPTO dated Jul. 10, 2019 for U.S. Appl. No. 15/477,929.

Final Office Action issued by the USPTO dated Jan. 7, 2020 for U.S. Appl. No. 15/477,929.

Advisory Action issued by the USPTO dated Apr. 15, 2020 for U.S. Appl. No. 15/477,929.

Communication Pursuant to Article 94(3) EPC issued to European counterpart Application No. 18723089.1 dated Nov. 30, 2023.

* cited by examiner

SKIN CARE COMPOSITION AND METHOD OF MAKING A SKIN CARE COMPOSITION

PRIORITY CLAIM

This application is a divisional of and claims priority to U.S. patent application Ser. No. 15/477,901 entitled SKIN CARE COMPOSITION AND METHOD OF MAKING A SKIN CARE COMPOSITION filed on Apr. 3, 2017; is a Continuation in Part of and claims priority to application Ser. No. 15/477,929 entitled METHOD FOR PROVIDING A CUSTOMIZED SKIN CARE PRODUCT TO A CONSUMER, filed on Apr. 3, 2017; is a Continuation in Part of and claims priority to application Ser. No. 15/477,965 entitled SKIN CARE COMPOSITION AND METHOD OF MAKING A SKIN CARE COMPOSITION filed on Apr. 3, 2017; and is a Continuation in Part of and claims priority to Ser. No. 16/580,498 entitled SYSTEM FOR FORMING A COSMETIC COMPOSITION filed on Sep. 24, 2019, which is a Continuation of application Ser. No. 15/477,992 filed on Apr. 3, 2017 now issued as U.S. Pat. No. 10,464,030 on Nov. 5, 2019 entitled SYSTEM FOR FORMING A COSMETIC COMPOSITION, the entirety of which are incorporated by reference herein.

FIELD OF TECHNOLOGY

The present disclosure is directed to a skin care composition and a method for treating skin conditions. More specifically, the present disclosure is directed to a skin care composition that has targeted active ingredients for treating target skin conditions and methods for creating customized skin care compositions.

BACKGROUND

Personalized skin care systems are desirable for consumers to provide a skin care composition that meets the skin care needs of the individual consumer.

Examples of personalized product lines include MaCrèmeSurMesure by Dr. Pierre Ricaud, Codage Paris, Customized TCM by Yue Sai, and prescription personalized serums (Re-Plasty) by Helena Rubinstein.

Helena Rubinstein uses a skinprofiler, a cutaneous analysis device that generates quantitative data to analyze a variety of skin attributes to diagnose consumers in-store and provide them with a personalized prescription product consisting of one universal serum base and single dose of concentrate. Helena Rubenstein products only consist of one single dose of concentrate containing actives that seek to address all skincare needs. In addition, the Helena Rubenstein product is a serum (aqueous based) product with water-soluble actives. The Helena Rubinstein skinprofiler measures elasticity, pigmentation, and texture of the skin and prescribes concentrate based on these results only.

Codage Paris has a custom-made skincare product line. Consumers use a website diagnostic tool in which they answer 23 questions that were developed by different specialists (including dermatologists, pharmacists, and nutritionists). Based on the results, Codage selects and formulates a composition in their existing line and sends consumers a final product within a week. The Codage Paris system does not include a base composition with personalized boosters. Codage Paris is a serum (aqueous based) product with water soluble actives. A diagnostic tool utilized for Codage is an online survey which automatically 'prescribes' a final product based on provided answers. The Codage Product provides a final pre-prepared formula for the consumer, which is sent directly from store to consumer, wherein no mixing is required.

MaCrèmeSurMesure by Dr. Pierre Ricaud similarly uses an online diagnostic tool in which consumers are given a questionnaire on their current skin and lifestyle. Based on the answers they provide, the website provides them with a cream base and combination of three active concentrates. Each "concentrate" for the MaCrèmeSurMesure only contains a single active ingredient. Typical "concentrates" for the MaCrèmeSurMesure products consist solely of pure extracts (100% active extract of chufa tubers, for example) and do not provide formulations. The MaCrèmeSurMesure product is aqueous based (water based moisturizing gel texture) and booster "concentrates" are water soluble extracts in aqueous form. The consumer is sent a kit with their products and mixes at home with a small mixing tool provided, which is not easily co-soluble. MaCrèmeSurMesure uses an online questionnaire to diagnose consumer.

Yue Sai is a Customized TCM Beauty Solution Ultimate Refining Serum that includes in-store formulations in China. The tailoring of the formulations were limited and included only aqueous based compositions.

There remains a need to provide an effective, skin care composition and method for treating skin that is customized to specific, individual customer target skin compositions and that is stable and efficacious.

BRIEF SUMMARY

In an exemplary embodiment, a skin care composition is provided. The skin care composition includes a base composition comprising one of an aqueous alcohol composition or an aqueous emulsion. The skin care composition further includes at least two booster compositions selected from the group consisting of a first grade exfoliating agent; a second grade exfoliating agent, the second grade exfoliating agent providing greater exfoliating than the first grade exfoliating agent; a first grade whitening agent; a second grade whitening agent, the second grade whitening agent providing greater whitening than the first grade whitening agent; a first grade anti-aging agent; and a second grade anti-aging agent, the second grade anti-aging agent providing greater anti-aging effects than the first grade anti-aging agent. The base composition and the at least two booster compositions have been mixed to form a composition that is stable and has efficacious concentrations of active ingredients corresponding to skin conditions of a consumer.

In another exemplary embodiment, a method for forming a skin care composition is provided. The method includes providing base composition comprising one of an aqueous alcohol composition or an aqueous emulsion. The method further includes providing at least two booster compositions selected from the group consisting of a first grade exfoliating agent; a second grade exfoliating agent, the second grade exfoliating agent providing greater exfoliating than the first grade exfoliating agent; a first grade whitening agent; a second grade whitening agent, the second grade whitening agent providing greater whitening than the first grade whitening agent; a first grade anti-aging agent; and a second grade anti-aging agent, the second grade anti-aging agent providing greater anti-aging effects than the first grade anti-aging agent. The at least two booster compositions and the base composition are mixed to form the skin care composition. The skin care composition corresponds to a skin condition of a consumer.

In another exemplary embodiment, a cosmetic dispensing system is provided. The system includes a base composition dispensing system comprising an aqueous alcohol composition and an aqueous emulsion. The system further includes a booster composition dispensing system comprising each of the following booster compositions: a first grade exfoliating agent; a second grade exfoliating agent; a first grade whitening agent; a second grade whitening agent; a first grade anti-aging agent; and a second grade anti-aging agent. The base composition dispensing system is arranged and disposed to provide one of the base compositions and the booster composition dispensing system arranged and disposed to provide at least two of the booster compositions.

The present disclosure is also directed to a method for cosmetic treatment of skin by applying the above-disclosed composition onto a surface of the skin.

Other features and advantages of the present invention will be apparent from the following more detailed description of the preferred embodiment which illustrates, by way of example, the principles of the invention.

BRIEF DESCRIPTION OF THE DRAWINGS

Wherever possible, the same reference numbers will be used throughout the drawings to represent the same parts.

DETAILED DESCRIPTION

All numbers expressing quantities of ingredients and/or reaction conditions are to be understood as being modified in all instances by the term "about", unless otherwise indicated.

The method and system, according to the present disclosure, includes a method wherein a comprehensive skin condition diagnosis practice that produces a targeted and efficacious product. The skin conditions of a consumer are analyzed either automatically, using a digital system or manually, for treatment with a skin care product. In one embodiment, consumers are provided with a questionnaire or shown representative photos of common skin conditions, wherein the consumers/patients provide information correlating to their individual skin care needs. In one embodiment, a skin care professional fills out a questionnaire based upon information from or about the consumer. Based on the correlation to the skin information obtained, the consumers are provided with a formulation including a base composition and boosters having actives, which form a stable composition having efficacious concentrations of active ingredients corresponding to the desired skin treatment.

Cosmetic Dispensing System

Figure 1:
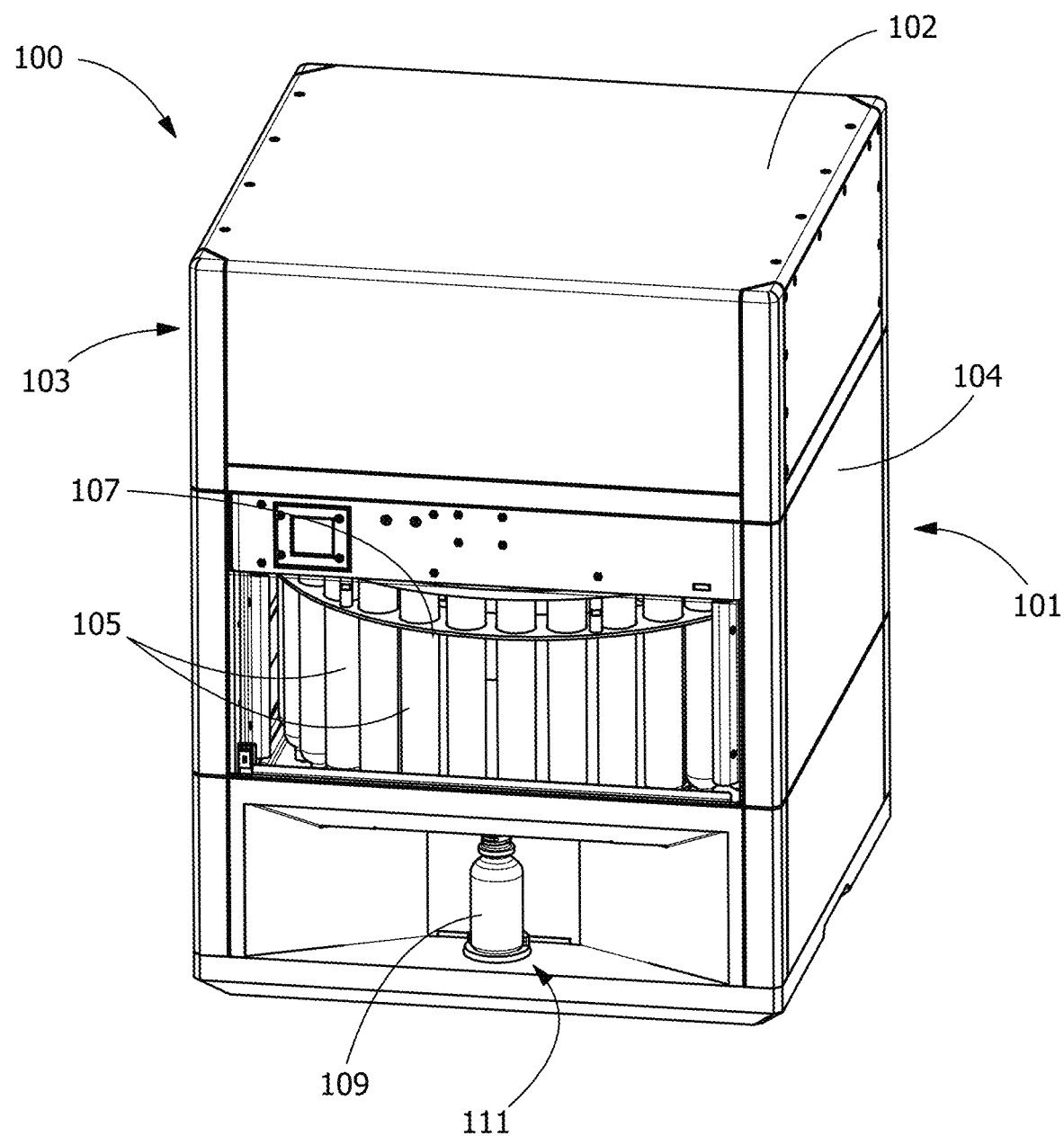
FIG. 1 illustrates a cosmetic dispensing system, according to an embodiment of the present disclosure.

FIG. 1 shows a cosmetic dispensing system 100, according to an embodiment of the present disclosure. The cosmetic dispensing system 100 includes a dispensing module 101 and a mixing module 103. A hinged lid 102 is hingeably attached to the outer housing 104. Dispensing module 101 provides a plurality of dispensing dosing receptacles 105 mounted on a carousel 107 that is rotatably driven to align the dispensing dosing receptacles 105 with a receiving receptacle 109 positioned in a receiving portion 111 of the cosmetic dispensing system 100. The carousel 107 and dispensing dosing receptacles 105 are driven such that, when a formula is provided, the dispensing dosing receptacles 105 are independently and sequentially aligned with the receiving portion 111 to provide ingredients from the dispensing dosing receptacles 105 to the receiving receptacle 109 to provide a skin care composition having a desired ingredient combination according to the formulation corresponding to the consumer skin condition and the compatibility profile between the base compositions and booster compositions in the formulation.

Method

Figure 2:
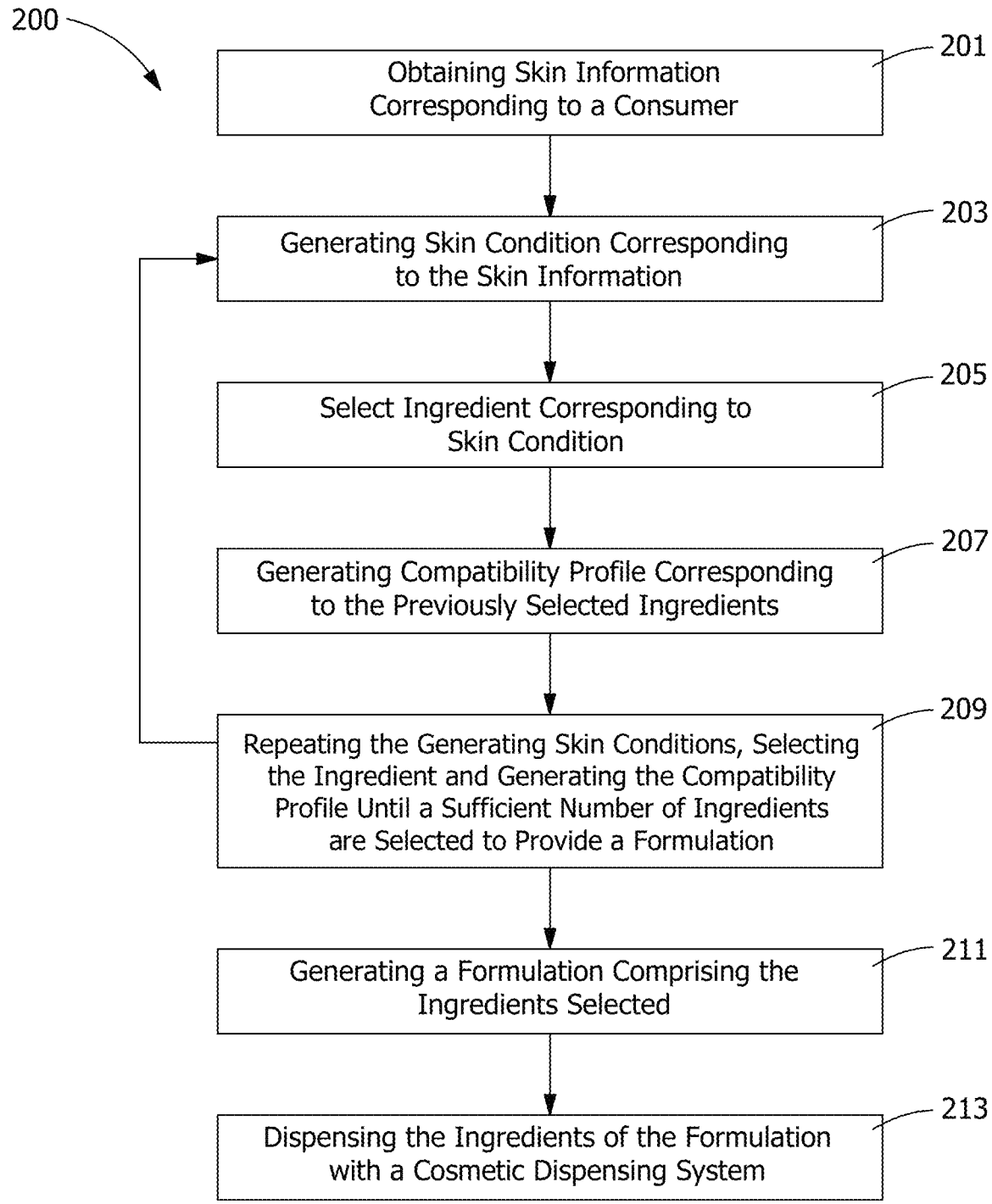
FIG. 2 a shows a method, according to an embodiment of the present disclosure.

FIG. 2 shows a method 200, according to the present disclosure. Method 200 includes obtaining skin information corresponding to a consumer (step 201). The method 200 further includes generating a skin condition corresponding to the skin information (step 203). Exemplary skin conditions for the first skin condition may include, but are not limited to skin requiring displaying some level of oiliness/dryness of the skin, requiring exfoliation (e.g., sensitivity), requiring lightening/whitening, and/or requiring anti-aging. One example may include a very dry skin condition and the utilization of base without drying components, but containing nourishing attributes. Furthermore, a very oily skin condition may utilize a hydroalcoholic base composition to help resolve this skin concern. The skin condition determined may also include a comparison of the numerical value, grade or other value indicator for the severity of the skin condition to determine which are suitable for treatment. In one particularly suitable embodiment, the correlation may include a consultation with a skin care professional, who may assist the consumer in determining the priority in which skin conditions may be present and/or desirably treated or may assist in comparing the severity score in determining the target skin conditions. For example, the skin condition may include, in one embodiment, a severity score to determine specific exfoliants, lightening agents, and/or anti-aging agents that correspond to the severity of the skin condition. The ingredients selected are dependent upon the skin condition. In one embodiment, the base composition is determined by the patient's skin type. For example, in another embodiment, the skin condition may include, a severity score to determine dosing or grade of exfoliating agents, lightening agents, and/or anti-aging agents that correspond to the severity of the skin condition or the priority of which the skin conditions should be treated. In one embodiment, the skin condition that is first utilized to select an ingredient includes a skin condition that corresponds to the skin condition of the consumer that has the greatest severity. In another embodiment, the skin condition utilized to select an ingredient may include a skin condition that relates to a condition that the consumer or skin care professional prioritizes as a greater need for treatment.

The skin condition may determine scores for categories of concern, such as, for example: pigmentation concern, sensitivity, complexion, wrinkles, texture, hydration, or oily/dry skin. In one particularly suitable embodiment, consultation from a skin care professional may be utilized. The skin care consultant may provide direction relating to the consumer's current regimen, skin type, skin concerns and lifestyle. To assess top skin concerns, diagnostic tools which may include, but are not limited to, a combination of a special prescription card (ranking of concerns) and reference pictures (skin atlas) are utilized. In addition, the skin information and the skin condition may be determined utilizing automated systems. For example, different devices for performing the skin diagnosis are readily understood in the art, such as the Lancome Diagnos ABS, HR Skinscope, Biotherm Bluesmart, Kiehl's Skinprofiler V.0, CA Dermanalyzer, and the Vichy Vichyconsult.

Figure 4:
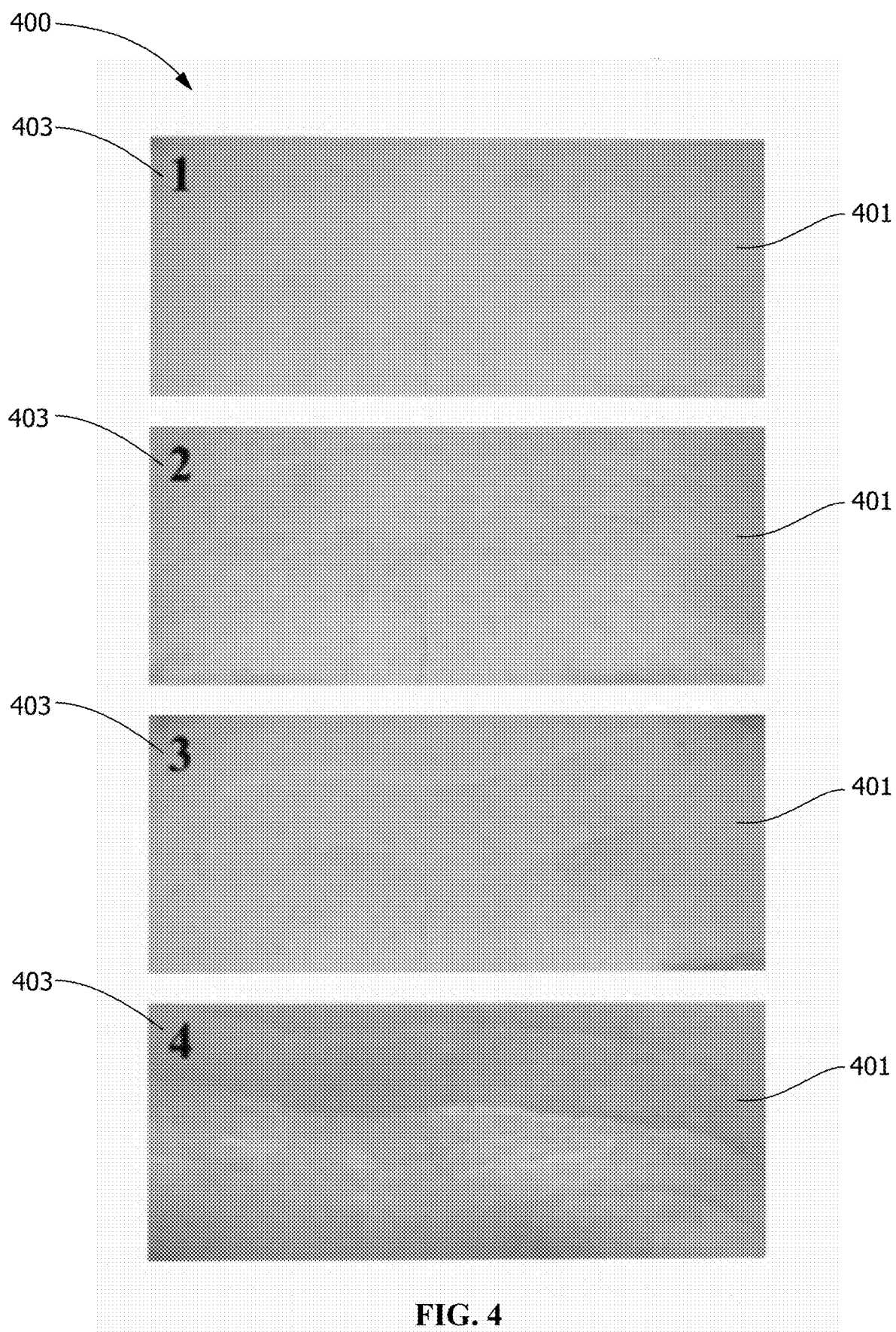
FIG. 4 shows a visual skin guide, according to an embodiment of the present disclosure.

In one embodiment, determining the skin information corresponding to a consumer is done via a visual display shown to the consumer. FIG. 4 shows an exemplary visual skin guide for obtaining skin information. Although FIG. 4 shows an example of visual skin guide, the present invention is not so limited and may include other types of visual displays and/or may provide skin information that correlates to other skin conditions. Other suitable types of visual displays include, but are not limited to, books, brochures and pamphlets including, but not limited to, pictures and/or description of skin condition and scale, clinical pictures, and photos taken with instrumental devices. The pictures and/or photos may include representations of skin conditions for panelists of different ethnicities and skin types. The visual display will correspond to the varying ethnicities and skin types. A selection of a specific visual display is made to consumer's ethnicity and/or skin types. The visual skin guide 400 is a device including visual representations 401, including, but not limited to, images, pictorial representations or similar visual devices that provide information regarding categorical skin conditions. In one embodiment, as shown in FIG. 4, each of the visual skin guides includes a plurality of visual representations of a categorical skin condition. In this embodiment, each of the visual representations corresponds to a severity score 403 for the categorical skin condition on the visual skin guide. As noted above, the severity score may be utilized to determine which type of ingredient may be added to the formulation or which grade of ingredient may be added to the formulation.

For example, as shown in FIG. 4, the visual representations may include photographs showing a particular category of skin condition of the categorical skin conditions including, but not limited to, skin brightness, aging, visibility of pores, skin texture, skin redness, skin firmness, skin tone evenness, or undesired skin pigmentation with a score that corresponds to severity. The severity score 403 may be a numerical value, grade value or any other suitable scoring that permits the determination of skin conditions. In one embodiment, the visual skin guide 400 includes four photographs of a particular skin condition scored numerically, for example, from 1 to 3 or from 1 to 4 or from 1 to 5 or from 1 to 10 or from 1 to 20 or from 1 to 100. In an alternate embodiment, the score includes a presence (i.e., yes) or absence (i.e., no) of a condition. The consumer, in one embodiment, may self-select the score that most closely corresponds to the skin condition that the consumer believes is present. This score is utilized in determination of the skin condition utilized to determine the corresponding ingredient.

In one embodiment, an information processing apparatus is configured to output a series of questions to the user to collect information about the consumer for collecting skin information. However, alternative embodiments are also available in which the user enters information directly into appropriate fields displayed on the information processing apparatus without being prompted by displayed questions in order to input the information into the information processing apparatus.

For example, the information processing apparatus may collect biographical information about the patient/consumer, such as name, age, skin tone, or any other information which may be used to generate a profile of the patient/consumer. For collecting skin information of the patient/consumer, a series of questions or fields are presented to the user to generate preferences on types of skin conditions the patient/consumer would like to address through the composition dispensed by the apparatus 100.

Referring again to FIG. 2, method 200 further includes selecting an ingredient corresponding to the skin condition (step 205). The ingredient includes a base composition or a booster composition that corresponds to the skin condition. For example, a booster containing alpha-hydroxy acid (e.g., lactic acid) active ingredients could be selected for a consumer with a skin conditioning denoting a high severity of skin dullness, while a booster containing 4-(2-hydroxyethyl)-1-piperazineethanesulfonic acid (HEPES) and hydroxyethyl urea could be selected for a consumer with a lower severity of skin dullness. In another instance, a booster containing C-beta-D-xylopyranoside-2-hydroxypropane (Pro-Xylane) could be selected for a selected for a consumer with a skin conditioning denoting a low severity of visible wrinkles. The selection of ingredients includes consideration of the previously selected ingredients and the compatibility profile of the previously selected ingredient. In addition, the selection of ingredient includes correlation of the skin condition to a specific ingredient or type of ingredient (e.g., exfoliating agents, whitening agents and/or anti-aging agents). Alternatively, the selection of ingredient may include a prioritization based upon other factors, such as consumer preference, or order of treatment from a skin care professional. In the case of the ingredient, the primary consideration of the selection of the ingredient is the skin condition, and its severity score or priority. In correlating the skin condition, the severity or priority includes a determination of the grade of ingredient. Grade, as utilized herein, includes an ingredient different efficacy for a particular condition. For example, a second grade exfoliation agent provides greater exfoliation than the first grade exfoliation agent. Likewise, such first and second grades are present for whitening and anti-aging agents. Additional considerations in determining the ingredient may further include the consumer tolerance for certain ingredients. For example, certain ingredients may result in skin effects that are undesirable to the consumer. For example, an ingredient with a higher grade than the individual could handle due to limited pre-exposure or high potency can cause the skin to show signs of redness or swelling. A booster containing the active ingredient retinol may be appropriate for a consumer displaying a high severity of visible signs of skin aging, while the same ingredient may be too harsh for the skin of a consumer with a low severity of visible signs of skin aging, or for a consumer who has sensitivity to the ingredient Retinol. For a consumer for whom Retinol is too harsh, using the ingredient may result in redness, peeling, or skin sensitivity. As such, a selection of a first grade ingredient may be prioritized over the selection of a second grade ingredient for an ingredient that produces undesirable skin effects to the consumer.

Referring again to FIG. 2, after the ingredient is determined, a compatibility profile is determined corresponding to the previously selected ingredients (step 207). The compatibility profile includes an inclusion or exclusion of additional ingredients to the formulation. That is, the compatibility profile provides acceptable combinations of booster composition and base composition combinations made with the previously selected ingredients that forms stable and efficacious skin care compositions. Compatibility for use in the compatibility profile includes, but is not limited to, combinations of base compositions and booster compositions that have 1) stability, including phase compatibility and solubility, 2) desirable pH, including a pH that does not result in esterification or similar incompatibility effects and 3) efficacy, including combinations of base compositions and booster compositions that retain the efficacy to provide the desired treatment for the skin condition determined in the formulation. "Stable", "Stability" and grammatical variations thereof, indicate a macroscopic homogeneous substance that doesn't have variation in texture or varying phases physically noticeable. In addition, microscopically the emulsion of the composition has the appearance of being homogeneous with the droplets and no dynamic changes in the microscope image. Examples of compatibility that result in a stable efficacious skin care composition include ingredients that have compatible pH, such that the combination of the ingredients do not provide esterification, crystallization, separation, and precipitation or other incompatible effects. In addition, compatibility may include ingredients that have compatible solubility that result in a stable emulsion, wherein the ingredients do not readily break into phases. In addition, compatibility may include ingredients that retain efficacy of individual ingredients when combined with the other ingredients remain present in the formula over time periods and exposures to varying temperature. For example, as an incompatible combination, a hydroalcoholic base is not compatible with retinol (as a second grade anti-aging agent) because the combination results in an incompatible pH and results in separation of phases. In another example, glycolic acid, lactic acid and sodium phytate (as a second grade exfoliation agent) are not compatible with the aqueous emulsion because the combination results in crystallization of the booster components. In another example, glycolic acid, lactic acid and sodium phytate (as a second grade exfoliation agent) are not compatible with tranexamic acid and urea (as a second grade whitening agent) because of a pH incompatibility.

Method 200 further includes repeating the generating skin conditions, selecting the ingredient and generating the compatibility profile until a sufficient number of ingredients are selected to provide a formulation (step 209). The sufficient number of ingredients includes a number of ingredients that address the skin concerns of the consumer based upon the skin information or include a number of ingredients corresponding to a skin care plan or regiment. For example, the skin care plan may include ingredients for treatment of the top three or four skin conditions, which correspond to three for four ingredients. However, the present disclosure is not so limited, as any number of skin conditions may be treated. In one embodiment, the skin care plan would correspond to at least three ingredients wherein the ingredients include a base composition and at least two booster compositions, the base composition and the booster compositions corresponding to skin conditions of the consumer for treatment.

Once the desired number of ingredients are selected, formulation including the ingredients is generated (step 211). In one embodiment, the formulation includes a base composition and at least two booster compositions. In another embodiment, the formulation includes a base composition and three booster compositions. Once the formulation is generated, the formulation, including the selected ingredients, is dispensed. The dispensing may be done manually or via an automated dispenser. After or during the dispensing the dispensed formulation may be mixed. Mixing may be mixed manually or automatically during or after the dispensing. For example, in one embodiment, as show in FIG. 1, the mixing may be provided by the mixing module 103 of cosmetic dispensing system 100. In this embodiment, the receiving receptacle 109 is filled by the dispensing module 101 and then inserted into the mixing module 103, wherein the receiving receptacle is mixed to provide a stable, homogeneous mixture.

Figure 3:
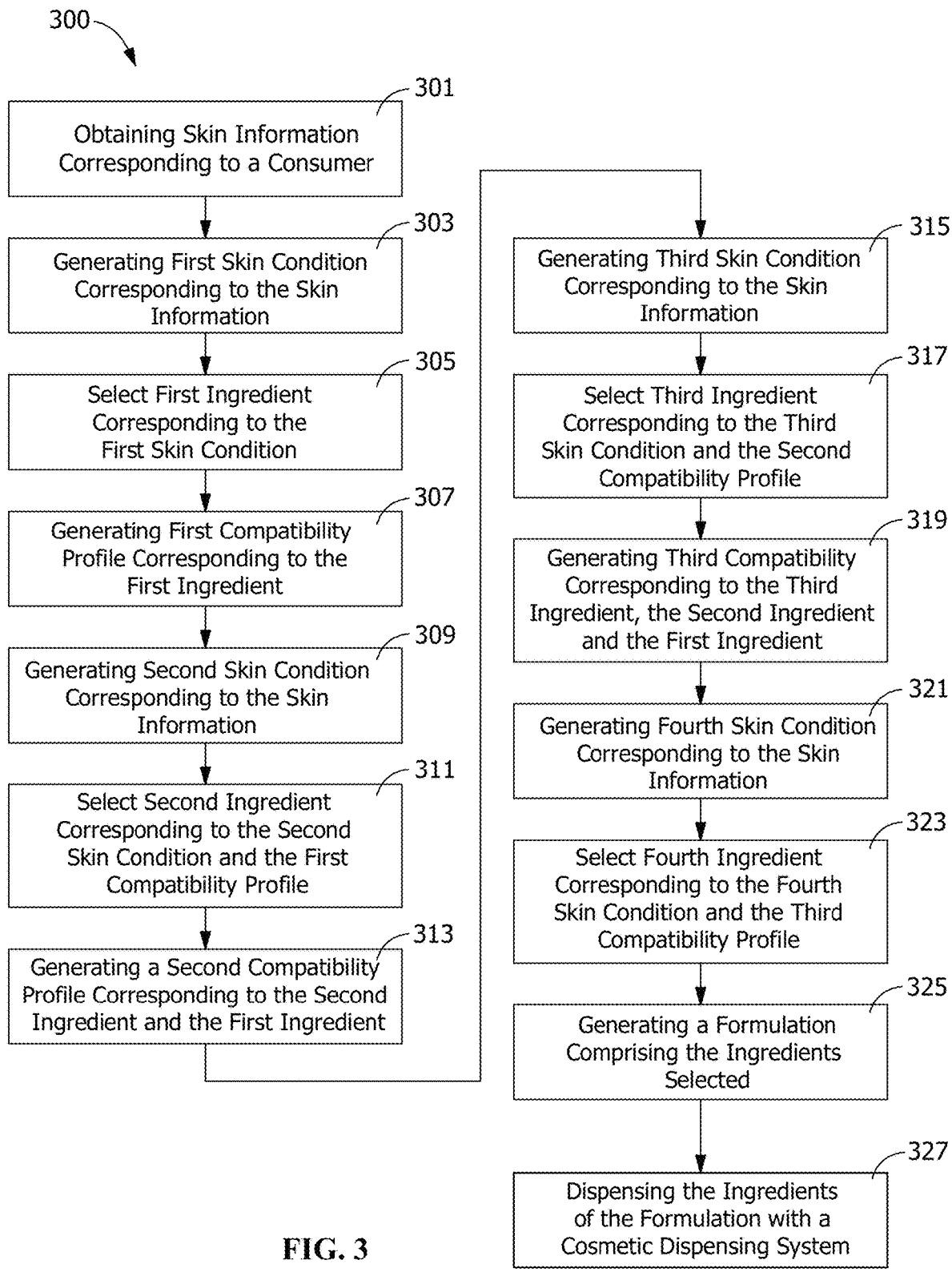
FIG. 3 a shows a method, according to an alternate embodiment of the present disclosure.

FIG. 3 shows an exemplary method 300, according to the present disclosure. Method 300 includes obtaining skin information corresponding to a consumer (step 301). The method 300 further includes generating a first skin condition corresponding to the skin information (step 303). The first skin condition is obtained as shown and described above with respect to FIG. 2.

Method 300 further includes selecting a first ingredient corresponding to the first skin condition (step 305). The first ingredient includes a base composition or a booster composition that corresponds to the first skin condition.

After the first ingredient is determined, a first compatibility profile is determined corresponding to the previously selected ingredients (step 307). The first compatibility profile includes an inclusion or exclusion of additional ingredients to the formulation. That is, the compatibility profile provides acceptable combinations of booster composition and base composition combinations made with the first ingredient that forms stable and efficacious skin care compositions.

Referring again to FIG. 3, method 300 further includes generating a second skin condition corresponding to the skin information (step 309). The second skin condition also preferably corresponds to the first skin condition. As noted above with respect to the skin condition, the second skin condition may include a severity or priority corresponding to the skin information or particular concerns of the consumer, whether determined automatically with the assistance of diagnostic tools or via a manual technique utilizing questionnaires or visual guides. Likewise, a skin care professional may assist or determine the skin care condition and/or the severity or priority of the skin condition as it relates to an ingredient to treat the skin condition. For example, the second skin condition may include a skin condition that the consumer or a skin care professional with the skin information determines to be the second most severe skin condition for treatment. Likewise, the second skin condition may include a skin condition that the consumer or a skin care professional with the skin information determines to be the skin condition that has the second highest priority for treatment.

Method 300 further includes selecting a second ingredient corresponding to the second skin condition (step 311). The selection of a second ingredient includes consideration of the previous selected ingredients and the compatibility profile of the previously selected ingredient. That is, the second ingredient selected includes a base composition or a booster composition that corresponds to the second skin condition that is not the first ingredient. In addition, the selection of a second ingredient includes correlation of the skin condition, including a prioritization. In correlating the skin condition to the second ingredient, the severity or priority includes a determination of the grade of ingredient. Accordingly, a second ingredient is selected, which includes a first or second grade of ingredient.

After the second ingredient is determined, method 300 further includes generating a second compatibility profile corresponding to the second ingredient and the first ingredient (step 313). Like the first compatibility profile, the second compatibility profile includes an inclusion or exclusion of additional ingredients to the formulation. That is, the second compatibility profile provides acceptable combinations of booster composition and base composition combinations made with the first ingredient and the second ingredient that form stable and efficacious skin care compositions.

Referring again to FIG. 3, method 300 further includes generating a third skin condition corresponding to the skin information (step 315). The third skin condition also preferably corresponds to the first skin condition and the second skin condition. As noted above with respect to the first condition, the third skin condition may include a severity or priority corresponding to the skin information or particular concerns of the consumer, whether determined automatically with the assistance of diagnostic tools or via a manual technique utilizing questionnaires or visual guides. Likewise, a skin care professional may assist or determine the skin care condition and/or the severity or priority of the skin condition as it relates to an ingredient to treat the skin condition. For example, the third skin condition may include a skin condition that the consumer or a skin care professional with the skin information determines to be the third most severe skin condition for treatment. Likewise, the third skin condition may include a skin condition that the consumer or a skin care professional with the skin information determines to be the skin condition that has the third highest priority for treatment.

Method 300 further includes selecting a third ingredient corresponding to the third skin condition (step 317). The selection of a third ingredient includes consideration of the previously selected ingredients and the compatibility profile of the previously selected ingredient. That is, the third ingredient includes a base composition or a booster composition that corresponds to the third skin condition that is not the first ingredient or the second ingredient. In addition, the selection of a third ingredient includes correlation of the skin condition, including a prioritization. In correlating the skin condition to the second ingredient, the severity or priority includes a determination of the grade of ingredient. Accordingly, a third ingredient is selected, which includes a first or second grade of ingredient.

After the third ingredient is determined, method 300 further includes generating a third compatibility profile corresponding to the third ingredient, the second ingredient and the first ingredient (step 319). Like the first compatibility profile and the second compatibility profile, the third compatibility profile includes an inclusion or exclusion of additional ingredients to the formulation. That is, the third compatibility profile provides acceptable combinations of booster composition and base composition combinations made with the first ingredient, the second ingredient and the third ingredient that form stable and efficacious skin care compositions.

Referring again to FIG. 3, method 300 further includes generating a fourth skin condition corresponding to the skin information (step 321). The fourth skin condition also preferably corresponds to the first skin condition, the second skin condition and the third skin condition. As noted above with respect to the first condition, the fourth skin condition may include a severity or priority corresponding to the skin information or particular concerns of the consumer, whether determined automatically with the assistance of diagnostic tools or via a manual technique utilizing questionnaires or visual guides. Likewise, a skin care professional may assist or determine the skin care condition and/or the severity or priority of the skin condition as it relates to an ingredient to treat the skin condition. For example, the fourth skin condition may include a skin condition that the consumer or a skin care professional with the skin information determines to be the fourth most severe skin condition for treatment. Likewise, the third skin condition may include a skin condition that the consumer or a skin care professional with the skin information determines to be the skin condition that has the fourth highest priority for treatment.

Method 300 further includes selecting a fourth ingredient corresponding to the fourth skin condition (step 317). The fourth ingredient includes a base composition or a booster composition that corresponds to the fourth skin condition that is not the first ingredient, the second ingredient or the third ingredient.

A formulation including the first ingredient, the second ingredient, the third ingredient, and the fourth ingredient is generated (step 325). The formulation includes a first ingredient, a second ingredient, a third ingredient, and a fourth ingredient that corresponds to a base composition and three booster compositions. Once the formulation is generated and communicated, the first ingredient, the second ingredient, the third ingredient, and fourth ingredient are dispensed with a cosmetic dispensing system. The dispensing may be done manually or via an automated dispenser. In addition, after or during the dispensing the formulation may be mixed. The mixing may be mixed manually or automatically during or after the dispensing. For example, in one embodiment, as show in FIG. 1, the mixing may be provided by the mixing module 103 of cosmetic dispensing system 100.

In one embodiment, a process or algorithm performed by the circuitry of an information processing apparatus for selecting the ingredients and determining the compatibility profile.

While the above has been described with respect to a first, second, third and fourth ingredient, other numbers of ingredients may be utilized, wherein additional skin conditions and additional compatibility profiles for determination of the formulation. For example, the first, second and third ingredients may correspond to a base composition and two booster compositions. Likewise, the first, second, third and fourth ingredients may include a fifth ingredient that includes a base composition and four booster compositions.

Formulation Ingredients

The formulation ingredients, according to the present disclosure, include ingredients selected from a base composition and at least two boosters that correspond to the skin condition. In one embodiment, the formulation ingredients include a first ingredient, a second ingredient, a third ingredient and a fourth ingredient that correspond to a base composition and three booster compositions. In this embodiment, each of the first ingredient, the second ingredient, the third ingredient and the fourth ingredient are independently selected from a base composition, which is one of an aqueous alcohol composition or an aqueous emulsion or a booster composition selected from the group consisting of a first grade exfoliating agent; a second grade exfoliating agent, the second grade exfoliating agent providing greater exfoliating than the first grade exfoliating agent; a first grade whitening agent; a second grade whitening agent, the second grade whitening agent providing greater whitening than the first grade whitening agent; a first grade anti-aging agent; and a second grade anti-aging agent, the second grade anti-aging agent providing greater anti-aging effects than the first grade anti-aging agent. The skin care composition formed from the formulation is stable and has efficacious concentrations of active ingredients corresponding to skin conditions of a consumer. Each of the ingredients is preferably added from a booster or base reservoir. In one embodiment, as shown in FIG. 1, booster compositions and base compositions are contained in dispensing dosing receptacles 105.

Exfoliation Booster Composition

In one embodiment, the ingredient selected may be an ingredient that provides exfoliation to improve skin appearance. As noted above, the selection of the ingredient may include a response to the consumer's skin condition, the previously selected ingredients, the compatibility profile of the already selected ingredients, and the identity of the previously selected ingredients. Active ingredients corresponding to exfoliation include one or more actives that provide exfoliation of the skin. The exfoliation booster composition includes a first grade exfoliation agent or a second grade exfoliation agent. The second grade exfoliation agent provides greater exfoliation than the first grade exfoliation agent. In the formulation and the selection of the individual ingredients, the first grade exfoliation agent and the second grade exfoliation agent are not the same.

For example, in one embodiment, the actives corresponding to an ingredient corresponding to a first grade exfoliation agent or a second grade exfoliation agent include one or more of glycolic acid, lactic acid, sodium phytate, 4-(2-hydroxyethyl)-1-piperazineethanesulfonic acid (HEPES), hydroxyethyl urea, salicylic acid, citric acid, capryloyl salicylic acid, and other components that provide improvement to skin appearance, and combinations thereof. Efficacious concentrations of the ingredients include concentration of active ingredients sufficiently high to provide exfoliation. For example, efficacious concentrations of from 1 wt % to about 15 wt % of glycolic acid, lactic acid, and sodium phytate; from 0.5 wt % to about 5 wt % 4-(2-hydroxyethyl)-1-piperazineethanesulfonic acid; from 2 wt % to about 10 wt % hydroexyethyl urea; from 0.05 wt % to about 0.04 wt % salicylic acid, from 1 wt % to about 15 wt % citric acid; and from 0.01 wt % to about 0.5 wt % capryloyl salicylic acid. In one embodiment, the active ingredients in a booster composition corresponding to the first grade exfoliation agent include 6% 4-(2-hydroxyethyl)-1-piperazineethane-sulfonic acid and 5.45% hydroxyethyl urea by weight of the skin care composition. In one embodiment, the active ingredients in a booster composition corresponding to the second grade exfoliation agent include 6.7% glycolic acid, 3.3% lactic acid and 1.7% sodium phytate by weight of the skin care composition.

Whitening Booster Composition

In one embodiment, the ingredient selected may be an ingredient that provides skin whiteness. As noted above, the selection of the ingredient may include a response to the consumer's skin condition, the previously selected ingredients, the compatibility profile of the already selected ingredients and the identity of the previously selected ingredients. Active ingredients corresponding to skin whiteness include one or more actives that provide improvement to skin whiteness. The whitening booster composition includes a first grade whitening agent or a second grade whitening agent. The second grade whitening agent provides greater whitening than the first grade whitening agent. In the formulation and the selection of the individual ingredients, the first grade whitening agent and the second grade whitening agent are not the same.

For example, in one embodiment, the actives corresponding to an ingredient corresponding to a first grade whitening agent or a second grade whitening agent include one or more of niacinamide, kojic acid, licorice extract, mulberry extract, tranexamic acid, urea, phenylethyl resorcinol, ascorbic acid, and other components that provide improvement to skin whiteness, any other suitable soluble/dispersible targeted active ingredient, and combinations thereof. Efficacious concentrations of the ingredients include concentration of active ingredients sufficiently high to provide whitening. For example, efficacious concentrations of from 0.01 wt % to about 2 wt % of licorice extract; from 0.001 wt % to about 0.5 wt % mulberry extract; from 0.25 wt % to about 10 wt % niacinamide; from 0.5 wt % to about 5 wt % koiic acid; from 0.01 wt % to about 1 wt % phenylethyl resorcinol; from about 0.1 wt % to about 4 wt % tranexamic acid; and from about 1 wt % to about 15 wt % acorbic acid. In one embodiment, the active ingredients in the first grade whitening agent include 0.1% licorice extract; and 0.0025% mulberry extract, by weight of the skin care composition. In one embodiment, the active ingredients in the second grade whitening agent include 3% niacinamide and 1% kojic acid by weight of the skin care composition. In one embodiment, the active ingredients in the second grade whitening agent include 0.5% phenylethyl resorcinol by weight of the skin care composition.

Anti-Aging Booster Composition

In one embodiment, the ingredient selected may be an ingredient that provides anti-aging. As noted above, the selection of the ingredient may include a response to the consumer's skin condition, the previously selected ingredients, the compatibility profile of the already selected ingredients and the identity of the previously selected ingredients. Active ingredients corresponding to anti-aging include one or more actives that provide improvement to skin appearance. The whitening booster composition includes a first grade anti-aging agent or a second grade anti-aging agent. The second grade anti-aging agent provides greater anti-aging effects than the first grade anti-aging agent. In the formulation and the selection of the individual ingredients, the first grade anti-aging agent and the second grade anti-aging agent are not the same.

For example, in one embodiment, the actives corresponding to an ingredient corresponding to a first grade anti-aging agent or a second grade anti-aging agent include one or more of C-beta-D-xylopyranoside-2-hydroxypropane (Pro-Xylane), retinol, peptides, caffeine, and other components that provide improvement to skin texture, any other suitable soluble/dispersible targeted active ingredient, and combinations thereof. Efficacious concentrations of the ingredients include concentration of active ingredients sufficiently high to provide anti-aging. For example, efficacious concentrations of from 0.5 wt % to about 10 wt % of C-beta-D-xylopyranoside-2-hydroxypropane; from 0.1 wt % to about 1.1 retinol; from 0.5 wt % to about 10 wt % ascorbic acid; from 0.1 wt % to about 1 wt % hyaluronic acid; from 0.01 wt % to about 1 wt % peptides; and from 0.1 wt % to about 1 wt % caffeine. In one embodiment, the active ingredients in the first grade anti-aging agent include 3.5% C-beta-D-xylopyranoside-2-hydroxypropane, by weight of the skin care composition. In one embodiment, the active ingredients in the second grade anti-aging agent include 0.1% or 0.3% or 0.5% or 1.0% retinol, by weight of the anti-aging booster composition.

Booster Additives

The booster compositions noted above may further include additional additives. For example, the booster compositions may include humectants, such as glycol and glycerin, soothing ingredients, essential oils, Vitamin E, emollients or other ingredients for skin enhancement, solubilization or other beneficial or efficacious purpose.

In one embodiment, the booster compositions are contained in dispensing dosing receptacles 105 (see FIG. 1). The concentrations of the ingredients for the booster ingredients (i.e., the exfoliating agents, the whitening agents and the anti-aging agents) in the dispensing dosing receptacles 105 is preferably at or near the solubility limits of the individual ingredients.

Base Composition

In addition to the plurality of booster compositions, base compositions are also provided.

Aqueous Alcohol Base Composition

One base composition suitable for use in the skin care composition includes an aqueous alcohol base composition. The aqueous composition includes an aqueous composition, comprising, consisting essentially of or consisting of an alcohol, such as ethanol or denatured alcohol. In one embodiment, the base composition includes an aqueous alcohol base composition comprising about 35 wt % alcohol, balance water.

Aqueous Emulsion Base Composition

One base composition suitable for use in the skin care composition includes an aqueous emulsion base composition. The aqueous emulsion base composition includes an aqueous composition, comprising, consisting essentially of or consisting of an emulsifier, such as polyacrylate crosspolymer-6. In one embodiment, the base composition includes an aqueous emulsion base composition comprising about 0.6 wt % polyacrylate crosspolymer-6. In another embodiment, the base composition includes an aqueous emulsion base composition comprising the following composition:

TABLE 1

| Name | Concentration (% by wt of base composition) | Concentration (% by wt of base composition) |
| --- | --- | --- |
| disodium EDTA | 0.1 | 0.05-0.2 |
| fatty compound | 2 | 0.5-3 |
| polymer 1 | 0.15 | 0.1-0.3 |
| polymer 2 | 0.5 | 0.1-1 |

TABLE 1-continued

| Name | Concentration (% by wt of base composition) | Concentration (% by wt of base composition) |
| --- | --- | --- |
| polymer 3 | 0.6 | 0.05-1.2 |
| preservative | 0.7 | 0.1-1.5 |
| silicon | 2 | 0.5-2.5 |
| solvent 1 | 3 | 1-4 |
| solvent 2 | 4 | 1-5 |
| solvent 3 | 3 | 0.5-4.5 |
| solvent 4 | 0.3 | 0.05-1 |
| surfactant | 0.5 | 0.1-1 |
| vitamin | 0.5 | 0.01-1 |
| water | 82.65 | QS |

The base compositions may include components suitable for providing skin care benefits, such as moisturization, protection of skin barrier, or other skin benefit.

In one embodiment, the base compositions are contained in dispensing dosing receptacles 105 (see FIG. 1). The concentration of the ingredients for the base compositions in the dispensing dosing receptacles 105 is preferably at the above indicated concentrations, wherein the base compositions include ranges of ingredients that permit dilution of the booster compositions to their efficacious concentrations, while maintaining the benefits of the booster composition.

Auxiliaries

In an embodiment, the composition of the disclosure may also contain adjuvants that are common in cosmetics, such as humectants, preserving agents, antioxidants, complexing agents, solvents, fragrances, bactericides, odor absorbers, vitamins, moisturizers, self-tanning compounds, and other active agents. The amounts of these various adjuvants are those conventionally used in the field under consideration, for example, from 0.01% to 20% of the total weight of the composition. In one embodiment, the additives or adjuvants would be added to the booster formulations to functionalize them for specific targeted treatments/needs.

Of course, a person skilled in the art will take care to choose this or these optional additional compounds so that the advantageous properties intrinsically attached to the composition, in accordance with the disclosure, are not, or not substantially, detrimentally affected by the envisaged addition or additions.

Needless to say, a person skilled in the art will take care to select this or of these optional additional compound(s), and/or the amount thereof, such that the advantageous properties of the composition, according to the disclosure, are not, or are not substantially, adversely affected by the envisaged addition.

The present disclosure includes a method and system wherein a comprehensive target skin condition diagnosis practice with a targeted and efficacious product formulated and delivered to the user. In one embodiment, a skin diagnosis/questionnaire, using visual aids, is completed to provide targeted skin care system to address the individual user's needs. The users are shown representative images of common skin conditions, wherein the users view the visual aids and correlate the visual aids with their individual skin care needs. Based on the correlation to the target skin conditions, the users get a customized cosmetic formulation having a base oil composition and at least two selected active booster compositions. In another embodiment, a digital image of a region of skin is analyzed to determine the individual user's skin care needs. An embodiment of a skin care system 500 is shown in FIG. 5.

Figure 5:
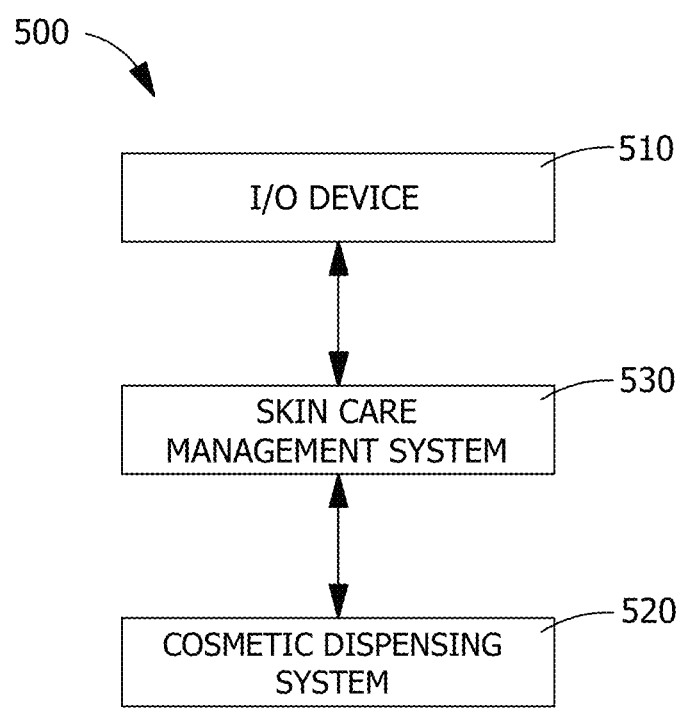
FIG. 5 is a block diagram of a skin care system including an input/output device, a cosmetic blender, and a skin care management system, including a microprocessor and a memory, according to an embodiment of the present disclosure.

In the example of FIG. 5, the skin care system 500 includes one or more input/output devices 510 configured to display information to a user and receive input from the user, one or more cosmetic dispensing systems 520 configured to dispense and/or mix a cosmetic formulation, and a skin care management system 530, coupled to the one or more input/output devices 510 and the one or more cosmetic dispensing systems 520, and including a microprocessor and a memory.

The skin care management system 530, is communicatively coupled to the one or more input/output devices 510 and to the one or more cosmetic dispensing systems 520. The skin care management system 530, may be wirelessly connected to the input/output devices 510 and the cosmetic dispensing systems 520 wirelessly (e.g., Bluetooth, internet, fiber optic, radio, and combinations thereof). In another embodiment, the skin care management system 530, may be connected to the input/output devices 510 and the cosmetic dispensing systems 520 via electrical links (e.g., wires). The skin care management system 530, may include, for example, a microcontroller (the microcontroller having an electronic processor, memory, and input/output components on a single chip or within a single housing). Alternatively, the skin care management system may include separately configured components. The skin care management system 530, may also be implemented using other components or combinations of components including, for example, a digital signal processor (DSP), an application specific integrated circuit (ASIC), a field programmable array (FPGA), or other circuitry. Depending on the desired configuration, the processor may include one or more levels of caching, such as a level cache memory, one or more processor caches, and registers. The example processor core may include an arithmetic logic unit (ALU), a floating point unit (FPU), or any combination thereof. The skin care management system 530, may also include a user interface, a communication interface, and other computer implemented devices for performing features not defined herein. In some examples, an interface bus for facilitating communication between various interface devices, computing implemented devices, and one or more peripheral interfaces to the microprocessor may be provided.

In an embodiment, a skin-care-management system includes circuitry configured to extract one or more significant features corresponding to one or more skin conditions captured in a plurality of digital images. Non-limiting examples of significant features corresponding to one or more skin conditions include pigmentation concern, sensitivity, complexion, wrinkles, texture, hydration, or oily/dry skin, which may correspond to skin requiring exfoliation, skin requiring whitening or skin requiring anti-aging treatment.

In an embodiment, circuitry includes, among other things, one or more computing devices such as a processor (e.g., a microprocessor, a quantum processor, qubit processor, etc.), a central processing unit (CPU), a digital signal processor (DSP), an application-specific integrated circuit (ASIC), a field programmable gate array (FPGA), and the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGAs, each having a plurality of programmable logic components.

In an embodiment, circuitry includes one or more electric circuits, printed circuits, flexible circuits, electrical conductors, electrodes, cavity resonators, conducting traces, ceramic patterned electrodes, electro-mechanical components, transducers, and the like.

In an embodiment, circuitry includes one or more components operably coupled (e.g., communicatively, electromagnetically, magnetically, ultrasonically, optically, inductively, electrically, capacitively coupled, wirelessly coupled, and the like) to each other. In an embodiment, circuitry includes one or more remotely located components. In an embodiment, remotely located components are operably coupled, for example, via wireless communication. In an embodiment, remotely located components are operably coupled, for example, via one or more communication modules, receivers, transmitters, transceivers, and the like.

In an embodiment, circuitry includes memory that, for example, stores instructions or information. Non-limiting examples of memory include volatile memory (e.g., Random Access Memory (RAM), Dynamic Random Access Memory (DRAM), and the like), non-volatile memory (e.g., Read-Only Memory (ROM), Electrically Erasable Programmable Read-Only Memory (EEPROM), Compact Disc Read-Only Memory (CD-ROM), and the like), persistent memory, and the like. Further non-limiting examples of memory include Erasable Programmable Read-Only Memory (EPROM), flash memory, and the like. In an embodiment, memory is coupled to, for example, one or more computing devices by one or more instructions, information, or power buses.

In an embodiment, circuitry includes one or more computer-readable media drives, interface sockets, Universal Serial Bus (USB) ports, memory card slots, and the like, and one or more input/output components such as, for example, a graphical user interface, a display, a keyboard, a keypad, a trackball, a joystick, a touch-screen, a mouse, a switch, a dial, and the like, and any other peripheral device. In an embodiment, circuitry includes one or more user input/output components that are operably coupled to at least one computing device configured to control (electrical, electro-mechanical, software-implemented, firmware-implemented, or other control, or combinations thereof) at least one parameter associated with, for example, determining one or more tissue thermal properties responsive to detected shifts in turn-ON voltage.

In an embodiment, circuitry includes a computer-readable media drive or memory slot that is configured to accept signal-bearing medium (e.g., computer-readable memory media, computer-readable recording media, and the like). In an embodiment, a program for causing a system to execute any of the disclosed methods can be stored on, for example, a computer-readable recording medium, a signal-bearing medium, and the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, and the like, as well as transmission type medium such as a digital or an analog communication medium (e.g., a fiber optic cable, a waveguide, a wired communications link, a wireless communication link (e.g., receiver, transmitter, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, and the like.

In an embodiment, circuitry includes acoustic transducers, electroacoustic transducers, electrochemical transducers, electromagnetic transducers, electromechanical transducers, electrostatic transducers, photoelectric transducers, radio-acoustic transducers, thermoelectric transducers, ultrasonic transducers, and the like.

In an embodiment, circuitry includes electrical circuitry operably coupled with a transducer (e.g., an actuator, a motor, a piezoelectric crystal, a Micro Electro Mechanical System (MEMS), etc.) In an embodiment, circuitry includes electrical circuitry having at least one discrete electrical circuit, electrical circuitry having at least one integrated circuit, or electrical circuitry having at least one application specific integrated circuit. In an embodiment, circuitry includes electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs.

In an embodiment, the skin care system 500 includes circuitry configured to generate severity information and cosmetic formulation compatibility information based on one or more inputs associated with extracting the one more significant features. Severity information is utilized to determine dosing or grade of exfoliating agents, lightening agents, and/or anti-aging agents that correspond to the severity of the skin condition or the priority of which the skin conditions should be treated. In one embodiment, the skin condition includes a skin condition that corresponds to the skin condition of the consumer that has the greatest severity. Non-limiting examples of severity information include level of pigmentation, the level of wrinkles on the skin of the consumer/patient.

The compatibility profile includes an inclusion or exclusion of additional ingredients to the formulation. The compatibility profile includes, but is not limited to, combinations of base compositions and booster compositions that have 1) stability, including phase compatibility and solubility, 2) desirable pH, including a pH that does not result in esterification or similar incompatibility effects and 3) efficacy, including combinations of base compositions and booster compositions that retain the efficacy to provide the desired treatment for the skin condition determined in the formulation.

In an embodiment, the skin care system additionally includes circuitry configured to virtually display user-specific compatible cosmetic formulation information based on at least one parameter associated with severity information and the cosmetic formulation compatibility information. For example, during operation, a user interacts with an application to enter user-specific skin conditions and levels of ingredient tolerance, and the application displays options for combinations of ingredients which are chemical compatible and meet the user-specific conditions. More specifically, for example, during operation, a user interacts with the tablet application to answer questions regarding personal levels of skin pigmentation, complexion, smoothness, wrinkles, sensitivities, ingredient tolerance, and hydration. The system then uses the user-specific skin-condition information (i.e., skin information) to produce a recommended combination of ingredients which specifically target the users levels and sensitivities, while also taking into account each time the chemical compatibilities between the ingredients to only recommend a stable formulation. The application displays these compatible cosmetic formulations to the user on the application. The user then selects from these personalized options which they prefer.

In the example of FIG. 5, a memory of the skin care management system 530 stores computer-readable instructions that, when executed by the electronic processor of the skin care management system 530, cause the skin care management system 530, and more particularly the electronic processor, to perform or control the performance of various functions or methods attributed to the skin care management system 530 herein (e.g., receive user input, receive uploaded data, determine a cosmetic formulation, determine a compatibility profile, determine severity scores, determine target skin conditions, communicate with a medical professional, establish secure communications, output information to the user, and combinations thereof). The memory may include any transitory, non-transitory, volatile, non-volatile, magnetic, optical, or electrical media, such as random access memory (RAM), read-only memory (ROM), non-volatile RAM (NVRAM), electrically erasable programmable ROM (EEPROM), flash memory, or any other digital or analog media. The functions attributed to the skin care management system 530 herein may be embodied as software, firmware, hardware, or any combination thereof.

In an example, the skin care management system 530 and the one or more input/output devices 510 (e.g., digital camera, cellular phone, tablet, personal digital assistant (PDA), a laptop, a computer, a wearable device, keyboard, sensors, and combinations thereof) may be embedded in a computing device and the one or more cosmetic dispensing systems 520 may be configured to communicate with the skin care management system 530. In this example, the one or more cosmetic dispensing systems 520 are configured to have wireless and/or wired communication with the skin care management system 530. For example, the one or more cosmetic dispensing systems 520 and the skin care management system 530 may be configured to communication via a network. In another example, skin care management system 530, may be remotely located on a server and may be configured to receive data from an external input/output device (e.g., a digital camera, a cellular phone, a tablet, a personal digital assistant (PDA), a laptop, a computer, a wearable device, a sensor), as well as, send data to a computing device as human readable format. The computing device may function as the device to display information to the user and/or receive input from the user. The computing device may include a cellular phone, a tablet, a personal digital assistant (PDA), a laptop, a computer, a wearable device, or other suitable computing device. The network may be a cloud computing network, a server, a wireless area network (WAN), a local area network (LAN), an in-vehicle network, or other suitable network.

The skin care management system 530, is configured to receive input from the user including skin information data associated with one or more skin conditions. The skin care management system 530, then determines one or more skin conditions based on the skin information. The skin care management system 530, then determines a severity score for each of the one or more skin conditions based on the skin information data. Based on the severity scores, the skin care management system 530 determines one or more targeted skin conditions and a cosmetic formulation to treat the targeted skin conditions. The skin care management system 530, additionally determines a compatibility score based on the interoperability of the components of the cosmetic formulation.

Figure 6:
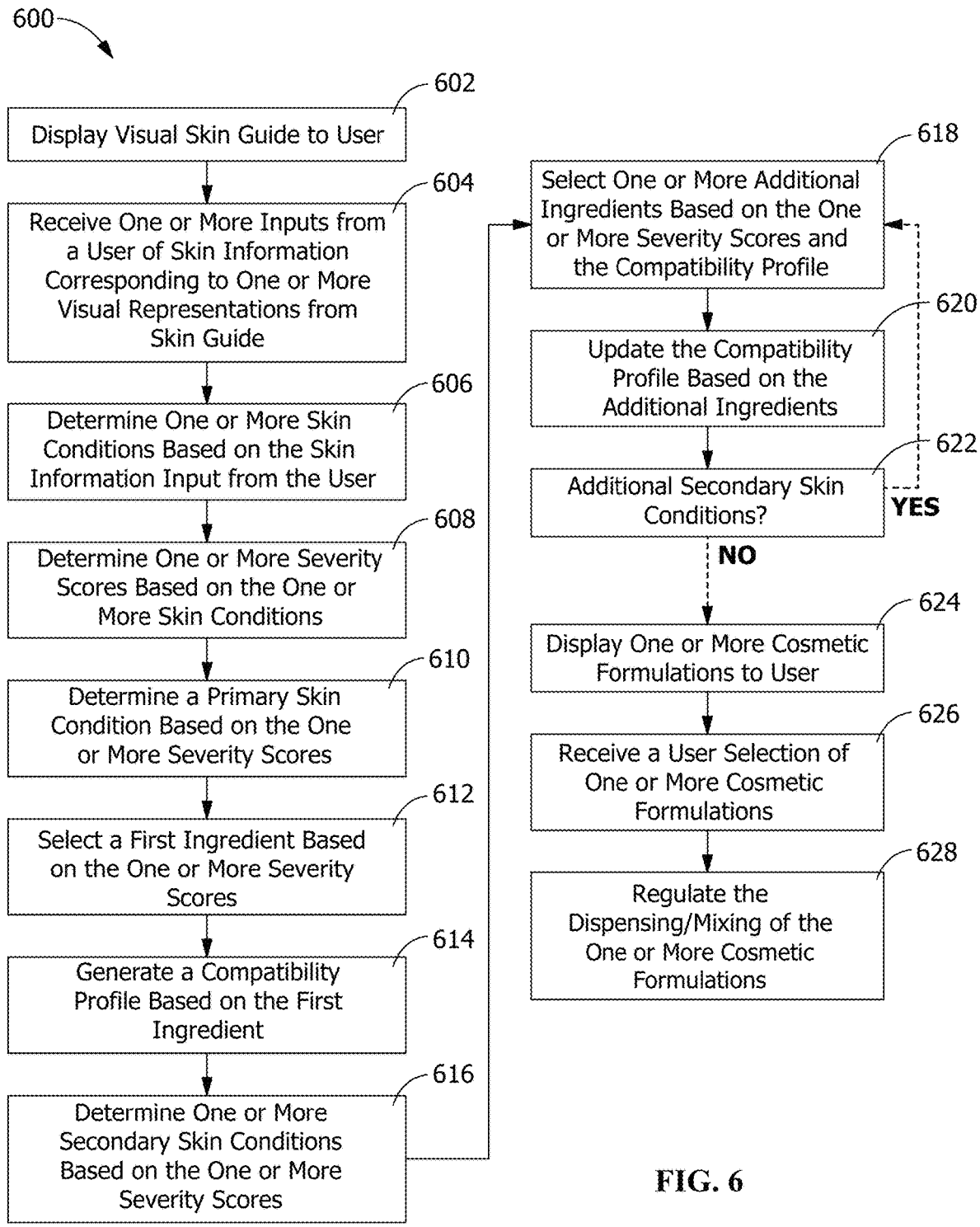
FIG. 6 is a flow chart of a method of managing a skin care system according to an embodiment of the present disclosure.

FIG. 6 is a flowchart of a method 600 of managing a skin care system 500. At block 602, the skin care management system 630 causes the input/output device (I/O device) 510 to display one or more visual skin guides to the user, each of the visual skin guides may include one or more visual representations of a categorical skin condition, each of the visual representations corresponding to a severity score for the categorical skin condition of the one or more visual skin care guides. In some embodiments, the visual skin care guide may include images of one or more skin conditions. In some embodiments, the visual skin guide may include a questionnaire with or without associated images. Alternatively, embodiments are also available in which the user enters information directly into appropriate fields displayed on the information processing apparatus without being prompted by displayed questions in order to input the information into the information processing apparatus. At block 604, the skin care management system 530 receives from the input/output device 510 one or inputs from the user including skin information corresponding to one or more visual representations of the categorical skin condition of the one or more visual skin guides. At block 606, the skin care management system 530 determines one or more skin conditions based on the skin information inputs from the user. At block 608, the skin care management system 430 determines one or more severity scores based on the one or more skin conditions. At block 610, the skin care management system 530 determines a primary skin condition based on the severity scores. At block 612, the skin care management system 530 selects a first ingredient based on the one or more severity scores. At block 614, the skin care management system 530 generates a compatibility profile based on the first ingredient. At block 616, the skin care management system 530 determines one or more secondary skin conditions based on the one or more severity scores. At block 618, the skin care management system 530 selects an additional ingredient based on the one or more severity scores and the compatibility profile. At block 620, the skin care management system 530 updates the compatibility profile based on the additional ingredient. At block 622, the skin care management system 530 determines if there are additional secondary skin conditions. If the skin care management system 530 determines there are additional secondary skin conditions, ("YES" at block 622), the skin care management system 530 selects an additional ingredient based on the one or more severity scores and the compatibility profile. In some embodiments, the number of additional ingredients is at least three. In one embodiment, the number of additional ingredients is three. At block 624, if the skin care management system 530 determined there are no additional secondary skin conditions, ("NO" at block 622), the skin care management system 530 displays one or more cosmetic formulations to the user. At block 636, the skin care management system 530 receives from the input/output device 510 a selection of one or more cosmetic formulations from the user. At block 638, the skin care management system 530 regulates the cosmetic dispensing system 520 to dispense and/or mix the selected ingredients to form the selected cosmetic formulation.

Figure 7:
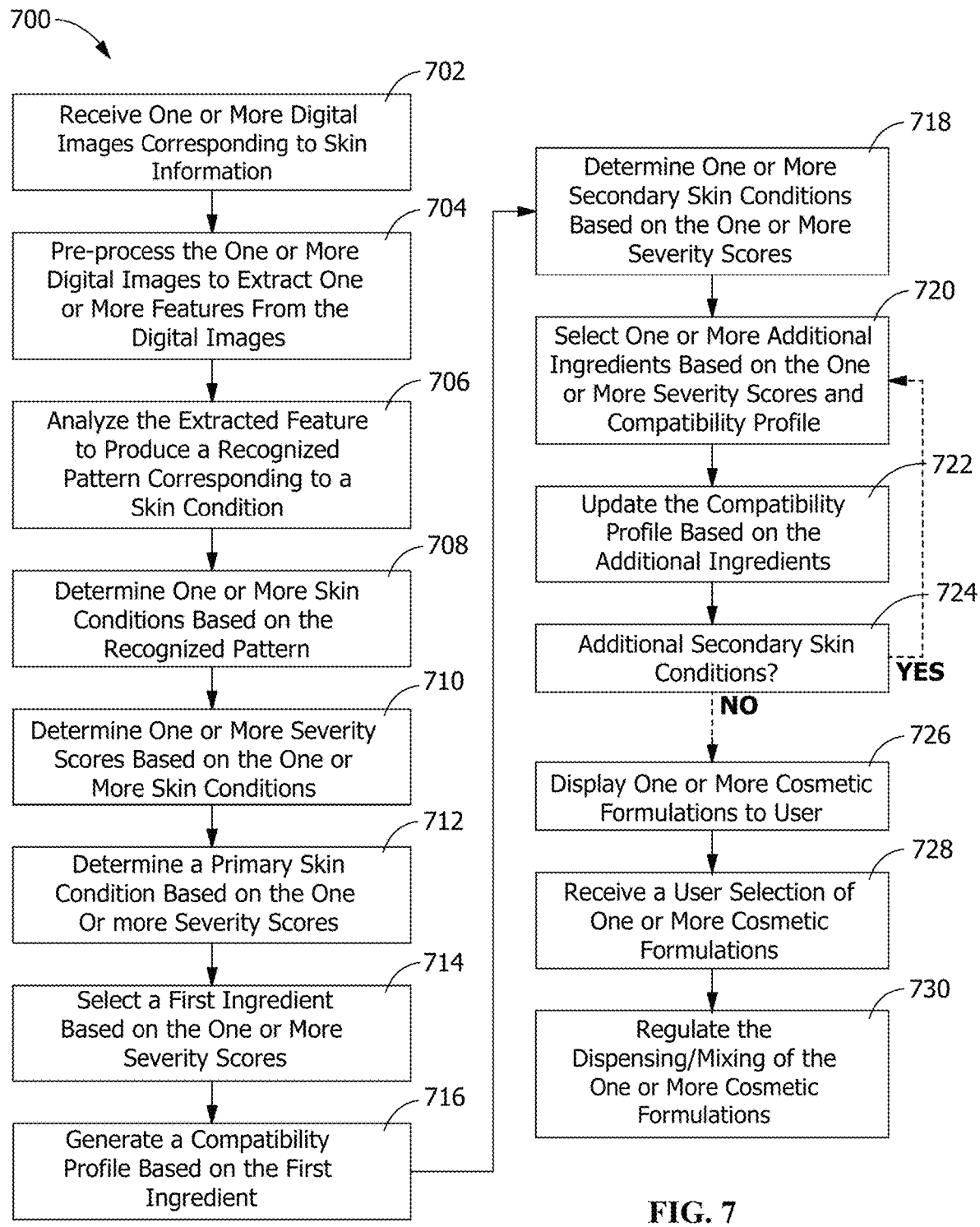
FIG. 7 is a flow chart of a method of managing a skin care system according to an embodiment of the present disclosure.

FIG. 7 is a flowchart of a method 700 of managing a skin care system 500. At block 702, the skin care management system 530 receives from the input/output device 510 one or more digital images corresponding to skin information from a user. At block 704, the skin care management system 530 pre-processes the one or more digital images to extract one or more features from the one or more images. At block 706, the skin care management system 530 analyzes the one or more extracted features to produce a recognized pattern corresponding to one or more skin conditions within the digital image. At block 708, the skin care management system 530 determines one or more skin conditions based on the recognized pattern. At block 710, the skin care management system 530 determines one or more severity scores based on the one or more skin conditions. At block 712, the skin care management system 530 determines a primary skin condition based on the one or more severity scores. At block 714, the skin care management system 530 selects a first ingredient based on the severity scores. At block 716, the skin care management system 530 generates a compatibility profile based on the first ingredient. At block 718, the skin care management system 530 determines one or more secondary skin conditions for treatment based on the one or more severity scores. At block 720, the skin care management system 530 selects an additional ingredient based on the one or more severity scores and compatibility profile. At block 722, the skin care management system 530 updates the compatibility profile based on the additional ingredient. At block 724, the skin care management system 530 determines if there are additional secondary skin conditions. If the skin care management system 530 determines there are additional secondary skin conditions, ("YES" at block 724), the skin care management system 530 selects an additional ingredient based on the one or more severity scores and the compatibility profile. At block 726, if the skin care management system 530 determined there are no additional skin conditions targeted for treatment, ("NO" at block 724), the skin care management system 530 displays one or more cosmetic formulations to the user. At block 728, the skin care management system 530 receives from the input/output device 510 a selection of one or more cosmetic formulations from the user. At block 730, the skin care management system 530 regulates the cosmetic dispensing system 520 to dispense and/or mix the selected ingredients to form the selected cosmetic formulation.

Figure 8:
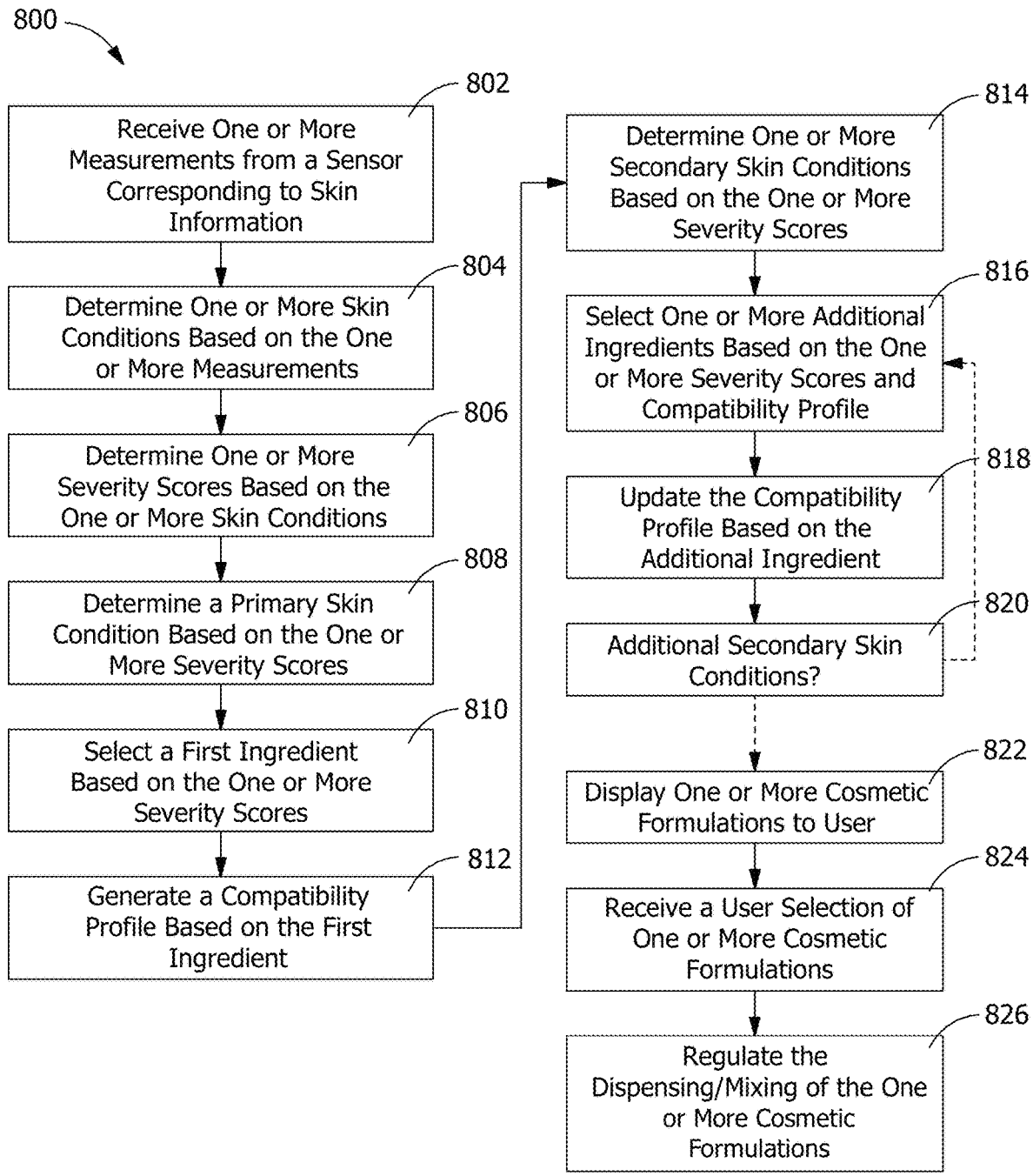
FIG. 8 is a flow chart of a method of managing a skin care system according to an embodiment of the present disclosure.

FIG. 8 is a flowchart of a method 800 of managing a skin care system 500. At block 802, the skin care management system 530 receives from the input/output device 510 one or more measurements from a sensor (e.g., magnetic, optical, non-optical, optoelectronic, electronic, and combinations thereof) corresponding to skin information from a user. At block 804, the skin care management system 530 determines one or more skin conditions based on the one or more measurements. At block 806, the skin care management system 530 determines one or more severity scores based on the one or more skin conditions. At block 808, the skin care management system 530 determines a primary skin condition based on the one or more severity scores. At block 810, the skin care management system 530 selects a first ingredient based on the one or more severity scores. At block 812, the skin care management system 530 generates a compatibility profile based on the first ingredient. At block 814, the skin care management system 530 determines one or more secondary skin conditions based on the one or more severity scores. At block 816, the skin care management system 530 selects an additional ingredient based on the one or more severity scores and the compatibility profile. At block 818, the skin care management system 530 updates the compatibility profile based on the additional ingredient. At block 820, the skin care management system 530 determines if there are additional secondary skin conditions. If the skin care management system 530 determines there are additional secondary skin conditions, ("YES" at block 820), the skin care management system 530 selects an additional ingredient based on the one or more severity scores and the compatibility profile. At block 822, if the skin care management system 530 determined there are no additional skin conditions targeted for treatment, ("NO" at block 820), the skin care management system 530 displays one or more cosmetic formulations to the user. At block 824, the skin care management system 530 receives from the input/output device 510 a selection of one or more cosmetic formulations from the user. At block 826, the skin care management system 530 regulates the cosmetic dispensing system 520 to dispense and/or mix the selected ingredients to form the selected cosmetic formulation.

Figure 9:
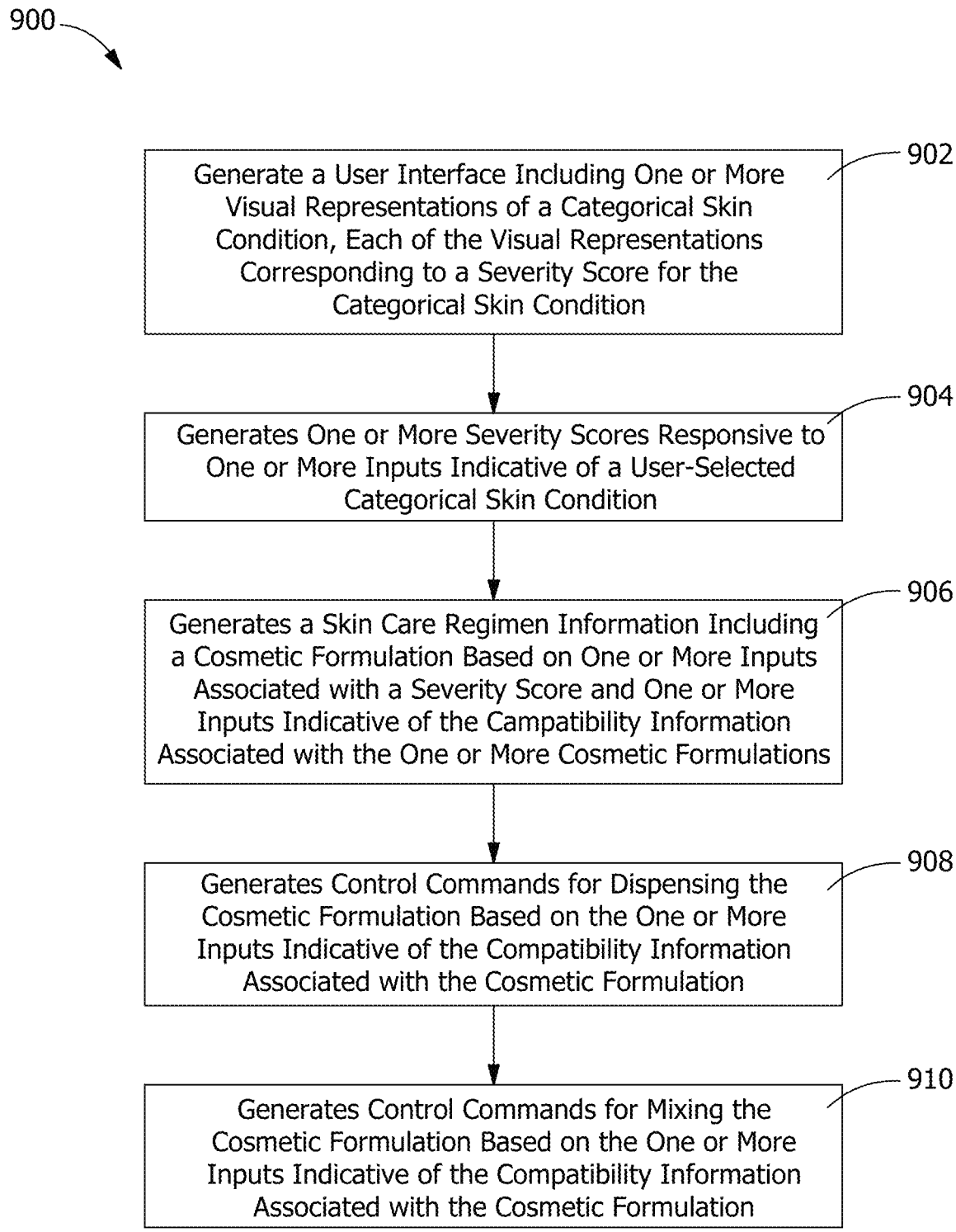
FIG. 9 is a flow chart of a method of managing a skin care system according to an embodiment of the present disclosure.

FIG. 9 is a flowchart of a method 900 of managing a skin care system 500. At block 902, the skin care management system 530 generates a user interface including one or more visual representations of a categorical skin condition, each of the visual representations corresponding to a severity score for the categorical skin condition. At block 904, the skin care management system 530 generates one or more severity scores responsive to one or more inputs indicative of a user-selected categorical skin condition. At block 906, the skin care management system 530 generates a skin care regimen information including a cosmetic formulation based on one or more inputs associated with a severity score and one or more inputs indicative of a compatibility information associated with one or more cosmetic formulations. At block 908, the skin care management system 530 generates control commands for dispensing the cosmetic formulation based on the one or more inputs indicative of the compatibility information associated with the cosmetic formulation. At block 910, the skin care management system 530 generates control commands for mixing the cosmetic formulation based on the one or more inputs indicative of the compatibility information associated with the cosmetic formulation.

Dispensing System

Figure 10:
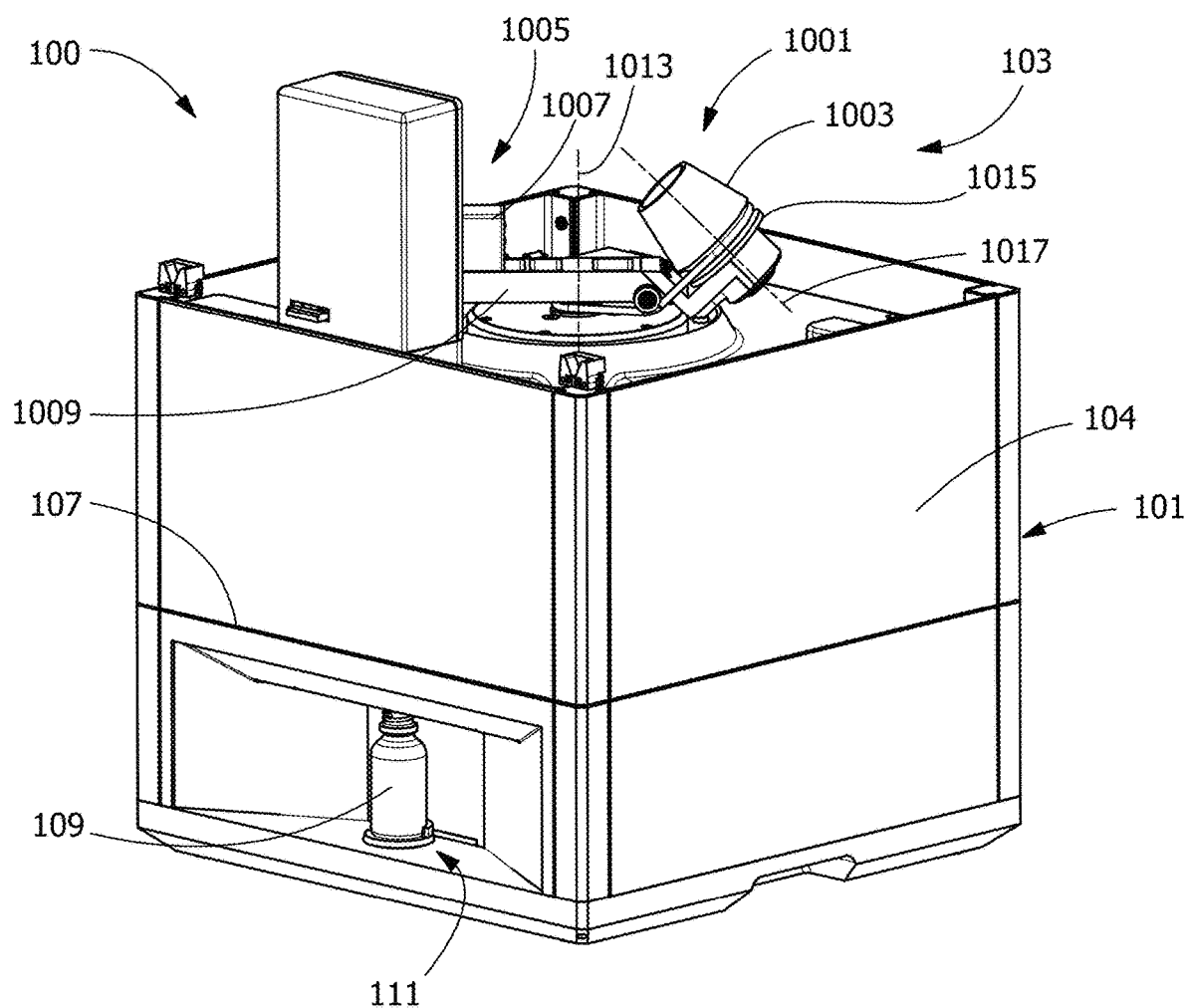
FIG. 10 illustrates a cosmetic dispensing system including the mixing module according to an embodiment with the hinged lid removed.

FIG. 10 shows a cosmetic dispensing system 100, as shown in FIG. 1, according to an embodiment with the hinged lid 102 removed. FIG. 10 shows mixing module 103. Mixing module 103 serves to mix the booster compositions and base composition dispensed to the receiving receptacle 109. The mixing module 103 includes a mixing side 1001 where a carrier 1003 that holds the receiving receptacle 109 and a balancing side 1005 which includes a counterweight 1007. The carrier 1003 is configured to receive the receiving receptacle 109, which has been filled by the dispensing module 101. To mix the formulation, the receiving receptacle 109 is filled with the dispensing module 101 and removed from the receiving portion and inserted into the carrier 1003. The receiving receptacle 109 is sized to fit within the carrier 1003 in a manner that prevents disengagement during mixing. A rotating support 1009 extends across the balancing side 1005 and the mixing side 1001. A drive motor (not shown) serves to drive the rotating support 1009 via a drive shaft in circular path about axis 1013. On the mixing side, the carrier 1003 is a rotating carrier which is driven by way of a flexible drive belt 1015 that is driven by a drive motor (not shown) to rotate the receiving receptacle 109 in carrier 1003 about an axis 1017 that is disposed at an angle with respect to axis 1013. The drive motor for rotating the rotating support 1009 and the carrier 1003 are the same and are connected via the flexible drive belt 1015.

Figure 11:
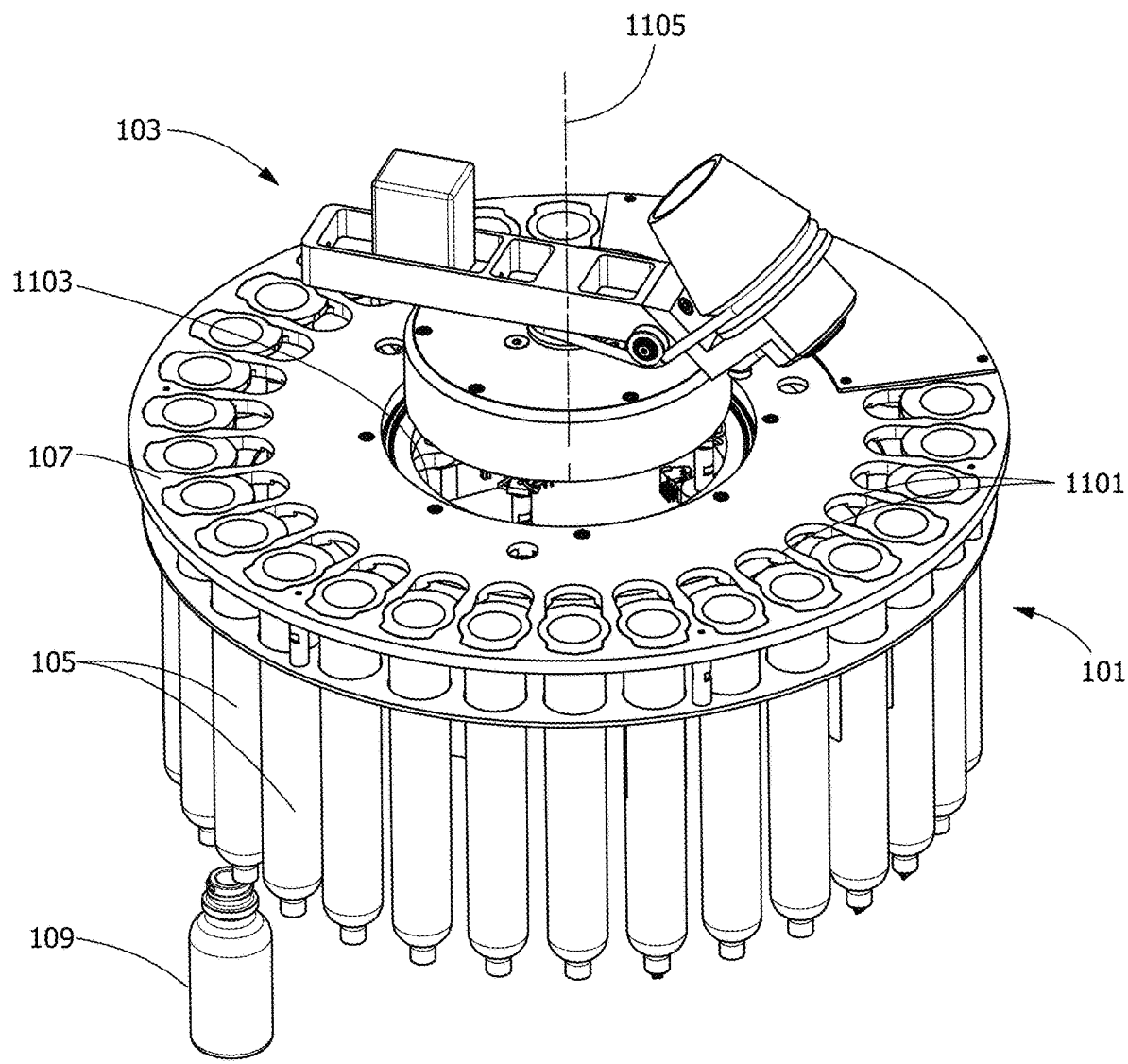
FIG. 11 illustrates a cosmetic dispensing system including the dispensing module according to an embodiment with the hinged lid and outer housing removed.

FIG. 11 show detailed views of the carousel 107 and dispensing dosing receptacles 105 of dispensing module 101 with the hinged lid 102 and the outer housing 104 removed. The carousel 107 includes slots 1100 for receiving the dispensing dosing receptacles 105. Additionally, a center portion 1103 attaches the interior section of the carousel 107 to a motor (not shown). The motor drives the carousel 107 in a circular path about axis 1105. The carousel 107 is driven so that the individual dispensing dosing receptacles 105 are aligned such that ingredients contained therein may be dispensed into the receiving receptacle 109. The carousel 107 is repeatedly driven with alignments of the dispensing dosing receptacles 105 and repeated dispensing until the formulation, including the base composition and booster compositions, is dispensed into the receiving receptacle 109.

Figure 12:
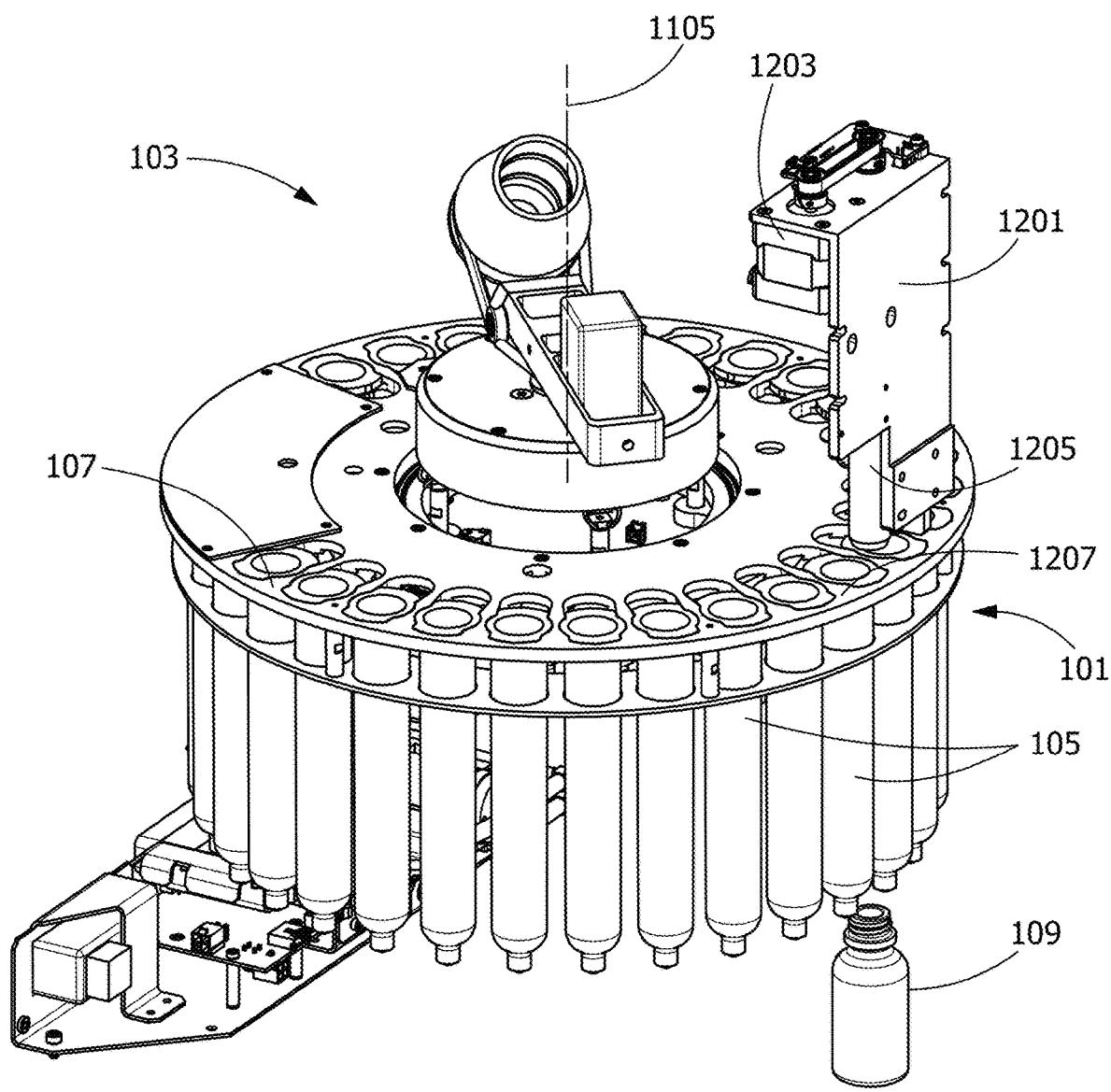
FIG. 12 illustrates a cosmetic dispensing system including the dispensing actuator according to an embodiment with the hinged lid and outer housing removed.

FIG. 12 show the dispensing module 105 including the dispensing actuator 1201. The dispensing detailed views of the carousel 107 and dispensing dosing receptacles 105 of dispensing module 101 with the hinged lid 102 and the outer housing 104 removed. FIG. 12 shows dispensing actuator 1201, which includes the dispensing motor 1203 and dispensing plunger 1205. The dispensing motor 1203 receives a signal from the CPU when the carousel 107 moves a dispensing dosing receptacle 105 into the dispensing region 1207. The dispensing motor 1203 activates to rotate transmitting spindle 1209 which causes rotation of receiving spindle 1211 through coupling by transfer belt 1213. Rotation of receiving spindle 1211 results in an up or down motion of plunger 1205. The dispensing plunger 1205 extends down into the dispensing receptacles 105 to result in a dispensing of the base composition or the booster composition into the receiving receptacle. The CPU is configured to detect when a target volume is reached with a closed loop using a load cell. The load cell (not shown) is disposed under the receiving receptacle. The load cell measures the actual volume dispensed by weighing the container holder being filled and causes a signal to be transmitted to the dispensing motor to cause the plunger 1205 to retract as soon as volume is reached. The formulation dispensed is a formulation corresponding to a compatibility profile and consumer skin conditions which, when mixed, forms a stable composition having efficacious concentrations of active ingredients.

Additionally the dispensing system 100 according to the present disclosure includes a drip-management system. The drip-management system includes a plurality of removable trays to accumulate rouge droplets, and an air-blowing system used to blow excess material from the tips of the dosing receptacles onto a removable pad.

Figure 13:
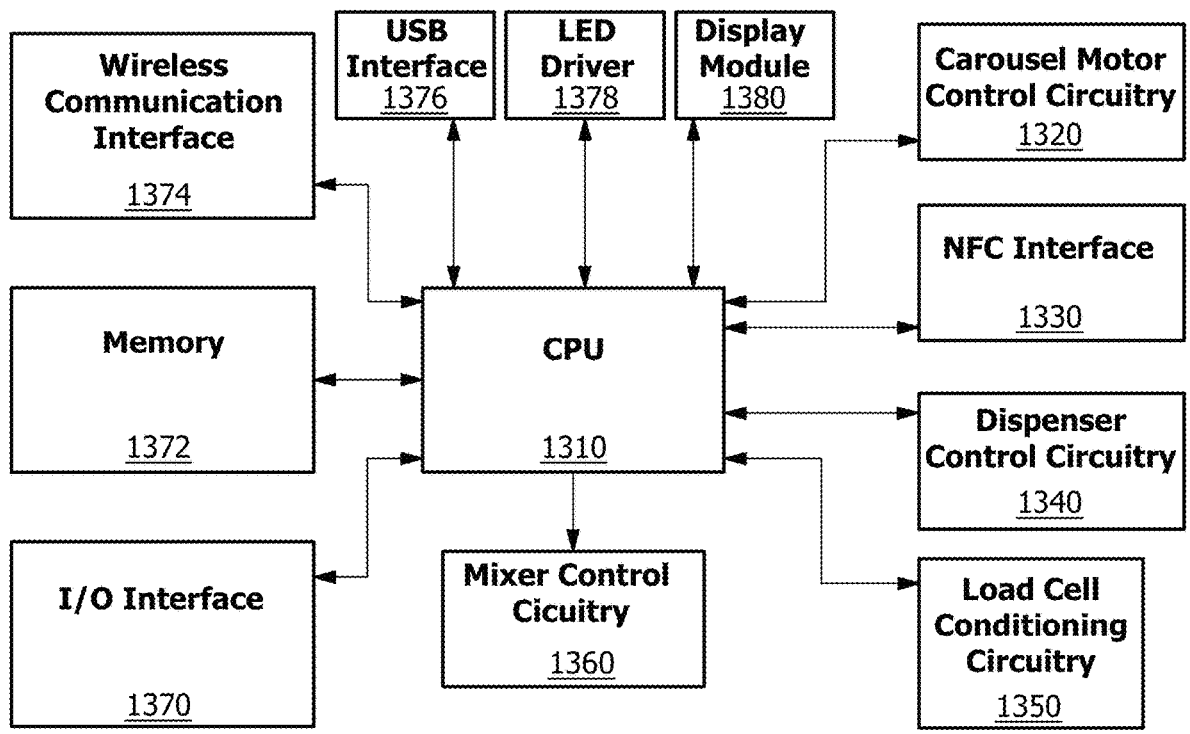
FIG. 13 shows a block diagram of the hardware included in the apparatus according to an embodiment.

FIG. 13 shows a block diagram of the hardware included in the apparatus. A central processing unit (CPU) 1310 provides primary control over the separate circuitry components included in the apparatus, such as the carousel motor control circuitry 1320, the NFC Interface 1330, the dispenser control circuitry 1340 (which includes the dispensing motor control circuitry and the inductive sensor circuitry), the load cell conditioning circuitry 1350, the mixer control circuitry 1360. The CPU 1310 also controls an optional input/output device (such as a keyboard or mouse), a memory 1380, the wireless communication interface circuitry 1374, a universal serial bus (USB) controller 1376, a LED driver 1378, and a display module 1380.

In an embodiment, any of the CPU 1310 or other components shown in FIG. 13 may be substituted with alternative circuitry elements. Examples of circuitry includes memory that, for example, stores instructions or information. Non-limiting examples of memory include volatile memory (e.g., Random Access Memory (RAM), Dynamic Random Access Memory (DRAM), or the like), non-volatile memory (e.g., Read-Only Memory (ROM), Electrically Erasable Program-mable Read-Only Memory (EEPROM), Compact Disc Read-Only Memory (CD-ROM), or the like), persistent memory, or the like. Further non-limiting examples of memory include Erasable Programmable Read-Only Memory (EPROM), flash memory, or the like. In an embodiment, memory is coupled to, for example, one or more computing devices by one or more instructions, information, or power buses.

In an embodiment, circuitry includes one or more computer-readable media drives, interface sockets, Universal Serial Bus (USB) ports, memory card slots, or the like, and one or more in-put/output components such as, for example, a graphical user interface, a display, a keyboard, a keypad, a trackball, a joystick, a touch-screen, a mouse, a switch, a dial, or the like, and any other peripheral device. In an embodiment, a module includes one or more user input/output components that are operably coupled to at least one computing device configured to control (electrical, electro-mechanical, software-implemented, firmware-implemented, or other control, or combinations thereof) at least one parameter associated with, for example, determining one or more tissue thermal properties responsive to detected shifts in turn-ON voltage.

In an embodiment, circuitry includes a computer-readable media drive or memory slot that is configured to accept signal-bearing medium (e.g., computer-readable memory media, computer-readable recording media, or the like). In an embodiment, a program for causing a system to execute any of the disclosed methods can be stored on, for example, a computer-readable re-cording medium, a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital or an analog communication medium (e.g., a fiber optic cable, a waveguide, a wired communications link, a wireless communication link (e.g., receiver, transmitter, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In an embodiment, circuitry includes acoustic transducers, electroacoustic transducers, electro-chemical transducers, electromagnetic transducers, electromechanical transducers, electrostatic transducers, photoelectric transducers, radioacoustic transducers, thermoelectric transducers, or ultrasonic transducers.

In an embodiment, circuitry includes electrical circuitry operably coupled with a transducer (e.g., an actuator, a motor, a piezoelectric crystal, a Micro Electro Mechanical System (MEMS), etc.) In an embodiment, circuitry includes electrical circuitry having at least one discrete electrical circuit, electrical circuitry having at least one integrated circuit, or electrical circuitry having at least one application specific integrated circuit. In an embodiment, circuitry includes electrical circuitry forming a general purpose computing device configured by a computer pro-gram (e.g., a general purpose computer configured by a computer program which at least partially carries out processes and/or devices described herein, or a microprocessor configured by a computer program which at least partially carries out processes and/or devices described here-in), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs.

Figure 14:
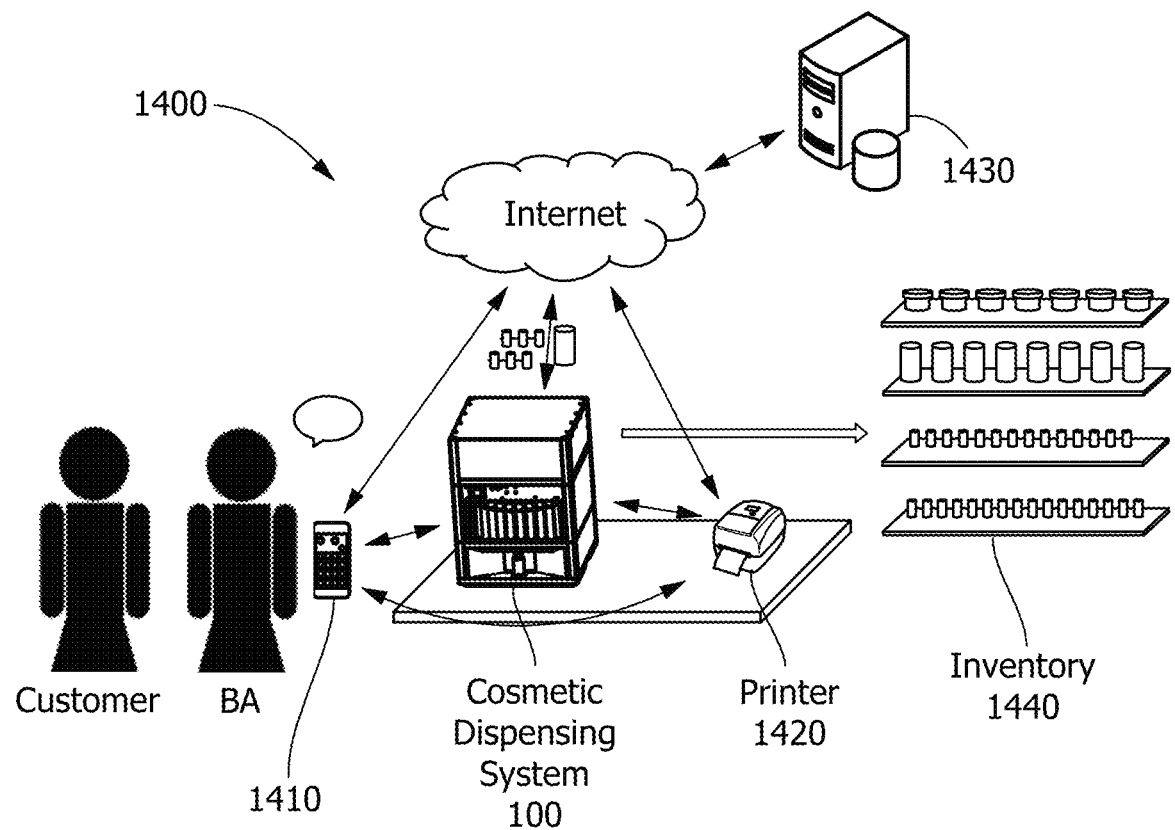
FIG. 14 shows an overall skin care system which implements the cosmetic dispensing system according to an embodiment.

FIG. 14 shows a skin care system 1400 which implements the cosmetic dispensing system 100 described above. As shown in FIG. 14, the system 1400 includes at least the cosmetic dispensing system 100, an information processing apparatus 1410, and a printer 1420. Optionally, the system may further include one or more external server devices or information processing apparatuses 1430 which are implemented as part of a cloud-computing environment. Furthermore, the system may optionally include inventory 1440 which is an inventory for booster compositions and base compositions to be inserted into the cosmetic dispensing system 100.

The information processing apparatus 1410 may be a personal computer (PC), a laptop computer, a PDA (Personal Digital Assistants), a smart phone, a tablet device, a UMPC (Ultra Mobile Personal Computer), a net-book, or a notebook type personal computer. In the below examples, the information processing apparatus 1410 is assumed to be a tablet device, such as an Apple iPad.

The printer 1420 may be any type of printing device or image forming device as understood in the art which has the capability of printing a label. In the below examples, the printing device is assumed to be a label printer, such as the Wireless Brother PTP750 W.

Each of the information processing apparatus 1410 and the printer 1420 are capable of performing wireless communication with the cosmetic dispensing system 100 by way of the Bluetooth interface on the cosmetic dispensing system 100. However, each of the information processing apparatus 1410 and the printer 1420 are also capable of having a wired connection to the cosmetic dispensing system 100 by way of the USB interface on the cosmetic dispensing system 100. Additionally, each device, including the cosmetic dispensing system 100, may communicate with each other and the external one or more devices through an internet connection via an 802.11 wireless connection to a wireless internet access point, or a physical connection to the internet access point, such as through an Ethernet interface. Each of the information processing apparatus 1410 and the printer 1420 are capable of performing wireless communication with each other through a Bluetooth connection or other wireless means as well.

The information processing apparatus 1410 is configured to receive information about a user for use in generating a recipe that will be used by the cosmetic dispensing system 100 to dispense a composition into the output container. The information processing apparatus 1410 may be operated by a skin care professional at the location, such as dermatologist office, where the dispensed composition is dispensed and provided to the customer user. However, the information processing apparatus 1410 can also be operated directly by the customer user.

In one embodiment, a process or algorithm performed by the circuitry of an information processing apparatus for selecting the ingredients and determining the compatibility profile.

In one embodiment, according to the present disclosure, the skin care composition is dispensed and/or mixed with the cosmetic dispensing system 100. The system includes a base composition dispensing system comprising an aqueous alcohol composition and an aqueous emulsion. The system further includes a booster composition dispensing system comprising each of the following booster compositions: a first grade exfoliating agent; a second grade exfoliating agent; a first grade whitening agent; a second grade whitening agent; a first grade anti-aging agent; and a second grade anti-aging agent. The base composition dispensing system is arranged and disposed to provide one of the base compositions and the booster composition dispensing system arranged and disposed to provide at least two of the booster compositions.

The following examples are intended to further illustrate the present disclosure. They are not intended to limit the disclosure in any way. Unless otherwise indicated, all parts are by weight.

EXAMPLES

TABLE 2 includes booster and base compositions utilized in examples and comparative examples.

TABLE 2

| Booster/ Base Code | Booster or Base Composition (% in Formulation) | Category |
|---|---|---|
| 1 | 6.7% glycolic acid, 3.3% lactic acid, 1.7% sodium phytate | Second Grade Exfoliation Agent |
| 2 | 6% 4-(2-hydroxyethyl)-1-piperazineethanesulfonic acid, 5.45% hydroxyethyl urea | First Grade Exfoliation Agent |
| 3 | 3% tranexamic acid, 1.25% urea | Second Grade Whitening Agent |
| 4 | 3% niacinamide, 1% kojic Acid | Second Grade Whitening Agent |
| 5 | 0.1% licorice extract, 0.0025% mulberry extract | First Grade Whitening Agent |
| 6 | 3.5% C-beta-D-xylopyranoside-2-hydroxypropane | First Grade Anti-Aging Agent |
| 7 | 0.1-1.0% retinol | Second Grade Anti-Aging Agent |
| 8 | 0.5% phenylethyl resorcinol | Second Grade Whitening Agent |
| B | hydroalcoholic base | Base |
| C | aqueous Emulsion base | Base |

Examples and comparative examples below are provided by the cosmetic dispending system as shown and described above. TABLE 3 includes the composition of Base B, the hydroalcoholic base, according to an embodiment of the disclosure.

TABLE 3

| Base B: Hydroalcoholic Base Composition | |
|---|---|
| Name | Concentration (% by wt of base composition) |
| Denatured Alcohol | 35% |
| Water | 65% |
| Total | 100% |

TABLE 4 includes the composition of Base C, the aqueous emulsion base, according to an embodiment of the disclosure.

TABLE 4

| Base C: Aqueous Emulsion Base Composition | |
|---|---|
| Name | Concentration (% by wt of base composition) |
| disodium EDTA | 0.1 |
| fatty compound | 2 |
| polymer 1 | 0.15 |
| polymer 2 | 0.5 |
| polymer 3 | 0.6 |
| preservative | 0.7 |
| silicon | 2 |
| solvent 1 | 3 |
| solvent 2 | 4 |
| solvent 3 | 3 |
| solvent 4 | 0.3 |
| surfactant | 0.5 |
| vitamin | 0.5 |
| water | 82.65 |

TABLE 5 includes inventive Examples of formulations including a first, second, third and fourth ingredient having a base composition and three booster compositions.

TABLE 5

| EXAMPLE | 1 | 2 | 3 |
|---|---|---|---|
| Reference Code | B (1 + 4 + 5) | B (1 + 4 + 6) | B (1 + 5 + 6) |
| Base | Hydro-alcoholic | Hydro-alcoholic | Hydro-alcoholic |
| Active Levels | Exfoliators | Exfoliators | Exfoliators |
| | 6.7% Glycolic Acid | 6.7% Glycolic Acid | 6.7% Glycolic Acid |
| | 3.3% Lactic Acid | 3.3% Lactic Acid | 3.3% Lactic Acid |
| | 1.7% Sodium Phytate | 1.7% Sodium Phytate | 1.7% Sodium Phytate |
| | Lightening Agents | Lightening Agents | Lightening Agents |
| | 3% Niacinamide | 3% Niacinamide | 0.1% Licorice Extract |
| | 1% Kojic Acid | 1% Kojic Acid | 0.0025% Mulberry Extract |
| | 0.1% Licorice Extract 0.0025% Mulberry Extract | Anti-Aging Agents 3.5% MA Pro-Xylane | Anti-Aging Agents 3.5% MA Pro-Xylane |
| pH | 3.73 | 3.53 | 3.71 |
| Stable | YES | YES | YES |

TABLE 6 includes inventive Examples of formulations including a first, second, third and fourth ingredient having a base composition and three booster compositions.

TABLE 6

| EXAMPLE | 4 | 5 | 6 |
|---|---|---|---|
| Reference Code | B (2 + 4 + 5) | B (2 + 4 + 6) | B (2 + 5 + 6) |
| Base | Hydro-alcoholic | Hydro-alcoholic | Hydro-alcoholic |
| Active Levels | Exfoliators | Exfoliators | Exfoliators |
| | 6% HEPES | 6% HEPES | 6% HEPES |
| | 5.45% | 5.45% | 5.45% |
| | Hydroxyethyl Urea | Hydroxyethyl Urea | Hydroxyethyl Urea |
| | Lightening Agent | Lightening Agent | Lightening Agent |
| | 3% Niacinamide | 3% Niacinamide | 0.1% Licorice Extract |
| | 1% Kojic Acid | 1% Kojic Acid | 0.0025% |
| | 0.1% Licorice Extract | Anti-Aging Agents | Mulberry Extract |
| | 0.0025% | 3.5% MA Pro-Xylane | Anti-Aging Agents |
| | Mulberry Extract | | 3.5% MA Pro-Xylane |
| pH | 5.56 | 5.27 | 5.66 |
| Stable | YES | YES | YES |

TABLE 7 includes inventive Examples of formulations including a first, second, third and fourth ingredient having a base composition and three booster compositions.

TABLE 7

| EXAMPLE | 7 | 8 | 9 |
|---|---|---|---|
| Reference Code | C(2 + 4 + 5) | C(2 + 5 + 6) | C(2 + 4 + 6) |
| Base | O/W Emulsion | O/W Emulsion | O/W Emulsion |
| Active Levels | Exfoliators | Exfoliators | Exfoliators |
| | 6% HEPES | 6% HEPES | 6% HEPES |
| | 5.45% | 5.45% | 5.45% |
| | Hydroxyethyl Urea | Hydroxyethyl Urea | Hydroxyethyl Urea |
| | Lightening Agent | Lightening Agent | Lightening Agent |
| | 3% Niacinamide | 0.1% Licorice Extract | 3% Niacinamide |
| | 1% Kojic Acid | 0.0025% | 1% Kojic Acid |
| | 0.1% Licorice Extract | Mulberry Extract | Anti-Aging Agent |
| | 0.0025% | Anti-Aging Agent | 3.5% MA Pro-Xylane |
| | Mulberry Extract | 3.5% MA Pro-Xylane | |
| pH | 5.43 | 5.43 | 5.44 |
| Stable | YES | YES | YES |

TABLE 8 includes inventive Examples of formulations including a first, second, third and fourth ingredient having a base composition and three booster compositions.

TABLE 8

| EXAMPLE | 10 | 11 | 12 |
|---|---|---|---|
| Reference Code | C(2 + 4 + 8) | C(2 + 5 + 8) | C(2 + 6 + 8) |
| Base | O/W Emulsion | O/W Emulsion | O/W Emulsion |
| Active Levels | Exfoliators | Exfoliators | Exfoliators |
| | 6% HEPES | 6% HEPES | 6% HEPES |
| | 5.45% | 5.45% | 5.45% |
| | Hydroxyethyl Urea | Hydroxyethyl Urea | Hydroxyethyl Urea |
| | Lightening Agent | Lightening Agent | Lightening Agent |
| | 0.5% Symwhite | 0.5% Symwhite | 0.5% Symwhite |
| | 3% Niacinamide | 0.1% Licorice Extract | Anti-Aging Agent |
| | 1% Kojic Acid | 0.0025% | 3.5% MA Pro-Xylane |
| | | Mulberry Extract | |
| pH | 5.53 | 5.59 | 5.59 |
| Stable | Yes | Yes | Yes |

TABLE 9 includes inventive Examples of formulations including a first, second, third and fourth ingredient having a base composition and three booster compositions.

TABLE 9

| EXAMPLE | 13-16 | 17-20 | 21-24 |
|---|---|---|---|
| Reference Code | C(4 + 5 + 7) | C(4 + 6 + 7) | C(5 + 6 + 7) |
| Base | Aqueous Emulsion | Aqueous Emulsion | Aqueous Emulsion |
| Active Levels | Lightening Agent 3% Niacinamide 1% Kojic Acid 0.1% Licorice Extract 0.0025% Mulberry Extract Anti-Aging Agent Retinol | Lightening Agent 3% Niacinamide 1% Kojic Acid Anti-Aging Agent 3.5% MA Pro-Xylane Retinol | Lightening Agent 0.1% Licorice Extract 0.0025% Mulberry Extract Anti-Aging Agent 3.5% MA Pro-Xylane Retinol |
| pH | 5.61 | 5.52 | 5.37 |
| Retinol 0.1% Stability (Ex. 13, 17 and 21) | Yes | Yes | Yes |
| Retinol 0.3% Stability (Ex. 14, 18 and 22) | Yes | Yes | Yes |
| Retinol 0.5% Stability (Ex. 15, 19 and 23) | Yes | Yes | Yes |
| Retinol 1.0% Stability (Ex. 16, 20 and 24) | Yes | Yes | Yes |

TABLE 10 includes inventive Examples of formulations including a first, second, third and fourth ingredient having a base composition and three booster compositions.

TABLE 10

| EXAMPLE | 25-28 | 29-32 | 33-36 |
|---|---|---|---|
| Reference Code | C(4 + 7 + 8) | C(5 + 7 + 8) | C(6 + 7 + 8) |
| Base | O/W Emulsion | O/W Emulsion | O/W Emulsion |
| Active Levels | Lightening Agents 0.5% Symwhite 3% Niacinamide 1% Kojic Acid Anti-Aging Agent Retinol | Lightening Agent 0.5% Symwhite 0.1% Licorice Extract 0.0025% Mulberry Extract Anti-Aging Agent Retinol | Lightening Agent 0.5% Symwhite Anti-Aging Agent 3.5% MA Pro-Xylane Retinol |
| pH | 5.4 | 5.12 | 5.44 |
| Retinol 0.1% Stability (Ex. 25, 29 and 33) | Yes | Yes | Yes |
| Retinol 0.3% Stability (Ex. 26, 30 and 34) | Yes | Yes | Yes |
| Retinol 0.5% Stability (Ex. 27, 31 and 35) | Yes | Yes | Yes |
| Retinol 1.0% Stability (Ex. 28, 32 and 36) | Yes | Yes | Yes |

TABLE 11 includes inventive Examples of formulations including a first, second, third and fourth ingredient having a base composition and three booster compositions.

TABLE 11

| Example | 37 | 38 | 39 |
|---|---|---|---|
| Base Active Levels | B (2 + 3 + 4) Hydro-alcoholic Exfoliators 6% HEPES 5.45% | B (2 + 3 + 5) Hydro-alcoholic Exfoliators 6% HEPES 5.45% | B (2 + 3 + 6) Hydro-alcoholic Exfoliators 6% HEPES 5.45% |

TABLE 11-continued

| Example | 37 | 38 | 39 |
|---|---|---|---|
| | Hydroxyethyl Urea Lightening Agents 3% Tranexamic acid 1.25% Urea 3% Niacinamide 1% Kojic Acid | Hydroxyethyl Urea Lightening Agents 3% Tranexamic acid 1.25% Urea 0.1% Licorice Extract 0.0025% Mulberry Extract | Hydroxyethyl Urea Lightening Agents 3% Tranexamic acid 1.25% Urea Anti-Aging Agents 3.5% MA Pro-Xylane |
| pH | 6.18 | 6.19 | 6.28 |
| No Retinol Stability | Yes | Yes | Yes |

TABLE 12 includes inventive Examples of formulations including a first, second, third and fourth ingredient having a base composition and three booster compositions.

TABLE 12

| Example | 40 | 41 | 42 |
|---|---|---|---|
| Base Active Levels | C(3 + 4 + 7) Aqueous Emulsion Lightening Agents 3% Tranexamic acid 1.25% Urea 3% Niacinamide 1% Kojic Acid Anti-Aging Agent Retinol | C(3 + 5 + 7) Aqueous Emulsion Lightening Agent 3% Tranexamic acid 1.25% Urea 0.1% Licorice Extract 0.0025% Mulberry Extract Anti-Aging Agent Retinol | C(3 + 6 + 7) Aqueous Emulsion Lightening Agent 3% Tranexamic acid 1.25% Urea Anti-Aging Agent 3.5% MA Pro-Xylane Retinol |
| pH | 6.45 | 6.93 | 6.65 |
| Retinol 0.1 | Yes | Yes | Yes |
| Retinol 0.5 | Yes | Yes | Yes |
| Retinol 0.3 | Yes | Yes | Yes |
| Retinol 1.0 | Yes | Yes | Yes |

TABLE 13 includes comparative Examples of formulations including a first, second, third and fourth ingredient having a base composition and three booster compositions.

TABLE 13

| | COMPARATIVE EXAMPLE | | |
|---|---|---|---|
| | C1 | C2 | C3 |
| Base | B | B | B |
| Booster | 1 + 4 + 7 | 1 + 5 + 7 | 2 + 4 + 7 |
| Stable | No | No | No |

TABLE 14 includes comparative Examples of formulations including a first, second, third and fourth ingredient having a base composition and three booster compositions.

TABLE 14

| | COMPARATIVE EXAMPLE | | |
|---|---|---|---|
| | C4 | C5 | C6 |
| Base | B | B | B |
| Booster | 1 + 5 + 7 | 1 + 6 + 7 | 1 + 3 + 7 |
| Stable | No | No | No |

TABLE 15 includes comparative Examples of formulations including a first, second, third and fourth ingredient having a base composition and three booster compositions.

TABLE 15

| | COMPARATIVE EXAMPLE | | |
|---|---|---|---|
| | C7 | C8 | C9 |
| Base | B | B | B |
| Booster | 1 + 3 + 5 | 1 + 3 + 6 | 2 + 5 + 7 |
| Stable | No | No | No |

TABLE 16 includes comparative Examples of formulations including a first, second, third and fourth ingredient having a base composition and three booster compositions.

TABLE 16

| | COMPARATIVE EXAMPLE | | |
|---|---|---|---|
| | C10 | C11 | C12 |
| Base | C | C | C |
| Booster | 1 + 4 + 5 | 1 + 5 + 6 | 1 + 4 + 6 |
| Stable | No | No | No |

TABLE 17 includes comparative Examples of formulations including a first, second, third and fourth ingredient having a base composition and three booster compositions.

TABLE 17

| | COMPARATIVE EXAMPLE | | |
|---|---|---|---|
| | C13 | C14 | C15 |
| Base | C | C | C |
| Booster | 1 + 4 + 8 | 1 + 5 + 8 | 1 + 6 + 8 |
| Stable | No | No | No |

TABLE 18 includes comparative Examples of formulations including a first, second, third and fourth ingredient having a base composition and three booster compositions.

TABLE 18

| | COMPARATIVE EXAMPLE | | | |
|---|---|---|---|---|
| | C16 | C17 | C18 | C19 |
| Base | C | C | C | C |
| Booster | 1 + 5 + 7 | 1 + 4 + 7 | 1 + 6 + 7 | 1 + 7 + 8 |
| Stable | No | No | No | No |

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for forming a skin care composition, the method comprising:
   receiving skin information and consumer preference information corresponding to an individual consumer;
   generating a skin condition attributed to the individual consumer corresponding to the skin information;
   providing a base composition at a location, the base composition comprising one of an aqueous alcohol composition or an aqueous emulsion;
   providing at least two booster compositions at the location, the at least two booster compositions selected from a booster panel which is the group consisting of:
   a first grade exfoliating agent;
   a second grade exfoliating agent, the second grade exfoliating agent providing greater exfoliating than the first grade exfoliating agent;
   a first grade whitening agent;
   a second grade whitening agent, the second grade whitening agent providing greater whitening than the first grade whitening agent;
   a first grade anti-aging agent; and
   a second grade anti-aging agent, the second grade anti-aging agent providing greater anti-aging effects than the first grade anti-aging agent;
   mixing the at least two booster compositions and the base composition at the location to form the skin care composition customized to cosmetically treat the skin condition of the individual consumer; and
   dispensing the skin care composition at the location into possession of the individual consumer at the location,
   wherein a first booster composition of the at least two booster compositions is selected from the booster panel by narrowing the booster panel based on effectiveness in addressing the skin condition and then prioritizing the booster panel based on the consumer preference information, and a second booster composition of the at least two booster compositions is selected by narrowing the booster panel based on compatibility with the first booster composition, then further narrowing the booster panel based on effectiveness in addressing the skin condition, and prioritizing the booster panel based on the consumer preference information such that the skin care composition corresponds to the skin condition attributed to the individual consumer and the consumer preference information corresponding to the individual consumer.

2. The method according to claim 1, wherein the at least two booster compositions include a first grade exfoliating agent comprising glycolic acid and lactic acid.

3. The method according to claim 1, wherein the at least two booster compositions include a second grade exfoliating agent comprising 4-(2-hydroxyethyl)-1-piperazineethanesulfonic acid and hydroxyethyl urea.

4. The method according to claim 1, wherein the at least two booster compositions include a first grade whitening agent comprising tranexamic acid and urea.

5. The method according to claim 1, wherein the at least two booster compositions include a second grade whitening agent comprising niacinamide and kojic acid.

6. The method according to claim 1, wherein the at least two booster compositions include a second grade anti-aging agent comprising phenylethyl resorcinol.

7. The method according to claim 1, wherein the at least two booster compositions include both a first grade whitening agent and a second grade whitening agent.

8. The method according to claim 1, wherein the at least two booster compositions include a first grade anti-aging agent comprising C-beta-D-xylopyranoside-2-hydroxypropane.

9. The method according to claim 1, wherein the at least two booster compositions include a second grade anti-aging agent comprising retinol.

\* \* \* \* \*